(12) United States Patent
Langlotz et al.

(10) Patent No.: US 10,975,177 B2
(45) Date of Patent: *Apr. 13, 2021

(54) PROCESS FOR PRODUCING A POLYACRYLAMIDE SOLUTION WITH INCREASED VISCOSITY

(71) Applicant: SOLENIS TECHNOLOGIES, L.P., Wilmington, DE (US)

(72) Inventors: Bjoern Langlotz, Ludwigshafen (DE); Linda Garella, Ludwigshafen (DE); Michael Guenter Braun, Ludwigshafen (DE); Juergen Daeuwel, Ludwigshafen (DE)

(73) Assignee: SOLENIS TECHNOLOGIES, L.P.

(*) Notice: Subject to any disclaimer, the term of this patent is extended or adjusted under 35 U.S.C. 154(b) by 32 days.

This patent is subject to a terminal disclaimer.

(21) Appl. No.: 16/087,472

(22) PCT Filed: Mar. 29, 2017

(86) PCT No.: PCT/EP2017/057410
§ 371 (c)(1),
(2) Date: Sep. 21, 2018

(87) PCT Pub. No.: WO2017/167803
PCT Pub. Date: Oct. 5, 2017

(65) Prior Publication Data
US 2019/0112399 A1   Apr. 18, 2019

(30) Foreign Application Priority Data
Mar. 29, 2016 (EP) ..................... 16162684

(51) Int. Cl.
| | |
|---|---|
| C08F 20/56 | (2006.01) |
| C12P 13/02 | (2006.01) |
| C08L 33/26 | (2006.01) |
| C08F 120/56 | (2006.01) |
| C08F 2/10 | (2006.01) |
| B01D 21/01 | (2006.01) |
| B01D 21/26 | (2006.01) |

(52) U.S. Cl.
CPC ............ *C08F 20/56* (2013.01); *C08F 2/10* (2013.01); *C08F 120/56* (2013.01); *C08L 33/26* (2013.01); *C12P 13/02* (2013.01); *B01D 21/01* (2013.01); *B01D 21/262* (2013.01); *C12Y 402/01084* (2013.01)

(58) Field of Classification Search
None
See application file for complete search history.

(56) References Cited

U.S. PATENT DOCUMENTS

| | | |
|---|---|---|
| 3,597,481 A | 8/1971 | Tefertiller et al. |
| 4,048,226 A | 9/1977 | Barber et al. |
| 4,248,968 A | 2/1981 | Watanabe et al. |
| 4,711,955 A | 12/1987 | Ward et al. |
| 5,525,711 A | 6/1996 | Hawkins et al. |
| 5,792,608 A | 8/1998 | Swaminathan et al. |
| 2004/0086986 A1 | 5/2004 | Banba et al. |
| 2005/0153421 A1 | 7/2005 | Murao et al. |
| 2011/0003355 A1 | 1/2011 | Clark et al. |
| 2011/0006258 A1 | 1/2011 | Oda et al. |
| 2014/0322777 A1 | 10/2014 | Clark et al. |

FOREIGN PATENT DOCUMENTS

| | | | |
|---|---|---|---|
| DE | 198 28 467 A1 | 12/1999 | |
| EP | 0 302 175 A2 | 2/1989 | |
| EP | 1 380 652 A1 | 1/2004 | |
| EP | 1 498 431 A1 | 1/2005 | |
| EP | 1498431 A1 * | 1/2005 | ............ C08F 20/56 |
| EP | 2 019 146 A1 | 1/2009 | |
| EP | 2 264 003 A1 | 12/2010 | |
| RU | 2196825 C2 | 1/2003 | |
| WO | WO 02/088372 A1 | 11/2002 | |
| WO | WO 2004/089518 A1 | 10/2004 | |
| WO | WO 2005/054488 A2 | 6/2005 | |
| WO | WO 2010/141780 A1 | 12/2010 | |
| WO | WO 2013/188844 A2 | 12/2013 | |

OTHER PUBLICATIONS

International Search Report dated Jul. 3, 2017, in PCT/EP2017/057410 filed Mar. 29, 2017.

Hatti-Kaul, R., "Downstream Processing in Industrial Biotechnology", Industrial Biotechnology, Sustainable Growth and Economic Success, Wiley-VCH Verlag GmbH & Co. KGaA, XP055284426, 2010, 43 pages.

* cited by examiner

Primary Examiner — Heidi Reese
(74) Attorney, Agent, or Firm — Lorenz & Kopf, LLP

(57) ABSTRACT

The present invention relates to a method for producing a polyacrylamide solution having increased viscosity. In particular, the present invention is related to the separation of a biocatalyst from an aqueous acrylamide solution prepared utilizing the biocatalyst prior to polymerization of the aqueous acrylamide solution to polyacrylamide. A polyacrylamide solution having increased viscosity is well suited to be used in tertiary oil recovery. Accordingly, the present application provides means and methods to crucially improve the quality of polyacrylamide solutions for use in tertiary oil recovery.

17 Claims, No Drawings
Specification includes a Sequence Listing.

PROCESS FOR PRODUCING A POLYACRYLAMIDE SOLUTION WITH INCREASED VISCOSITY

FIELD OF THE INVENTION

The present invention relates to methods for producing a polyacrylamide solution having increased viscosity as compared to a reference solution and polyacrylamide solutions obtainable by such methods, wherein the polyacrylamide solution is produced by polymerization of an aqueous acrylamide solutions having an $OD_{600}$ of equal to or less than 0.6, preferably equal to or less than 0.4, more preferably equal to or less than 0.3, even more preferably equal to or less than 0.2, still more preferably equal to or less than 0.15, still more preferably equal to or less than 0.12, still more preferably equal to or less than 0.1, still more preferably equal to or less than 0.075, most preferably equal to or less than 0.05. Moreover, the present invention relates to an acrylamide solution having an $OD_{600}$ in the range of 0.6 to 0.001 and the use of such acrylamide solutions for the manufacture of a polyacrylamide solution having increased viscosity.

BACKGROUND OF THE INVENTION

The following discussion of the background of the invention is merely provided to aid the reader in understanding the invention and is not admitted to describe or constitute prior art to the present invention.

Polyacrylamides are widely used as flocculates and thickener in water treatment and processes like paper making. Polyacrylamide can be supplied in a powder or liquid form, with the liquid form being subcategorized as solution and emulsion polymer. Another common use of polyacrylamide and its derivatives is in subsurface applications such as enhanced oil recovery. If after primary and secondary oil recovery further promotion with conventional methods is no longer conducive, methods to increase the mobility of the oil in order to enhance the extraction outcome are used in tertiary oil recovery. One of these methods is the injection of aqueous solutions containing polymers such as polyacrylamide, which allows another 5% to 15% of the reservoir's oil to be recovered (K. C. Taylor, J. A. Nasr-El-Din, *J. Petr. Sci. Ang.* 1998, 19, 265-280, K. C. Taylor, Annual Transactions of the Nordic Rheology Society, Vol. 11, 2003).

The raw material for polyacrylamide is typically its monomer acrylamide. In principal, there exist two different methods to produce acrylamide in industrial scales: Chemical synthesis and biological synthesis, wherein the biological synthesis methods are more and more on the rise due to milder reaction conditions and inherent process safety. Due to the milder reaction conditions the absence of copper catalyst and the quantitative conversion of the nitrile, expensive downstream processing steps such as distillation or ion exchange can be avoided in the biological synthesis, thus resulting in cheaper plants with drastically reduced plant footprint.

Both synthesis methods use acrylonitrile as starting substance. While the chemical synthesis method uses copper catalysts (U.S. Pat. Nos. 4,048,226, 3,597,481), the biological synthesis method employs biocatalysts to hydrate acrylonitrile in order to obtain acrylamide. Generally such biocatalysts are microorganisms which are able to produce the enzyme nitrile hydratase (IUBMB nomenclature as of July 2013: EC 4.2.1.84; CAS-No. 2391-37-5; also referred to as, e.g., NHase). Nitrile hydratase producing microorganisms are largely distributed in the environment and comprise, inter alia, representatives of the genus *Rhodococcus* (e.g., *Rhodococcus rhodochrous, Rhodococcus erythropolis, Rhodococcus ruber*), *Nocardia* (e.g., *Nocardia transvalensis*), *Pseudonocardia* (e.g., *Pseudonocardia thermophila*), *Bacillus* (e.g., *Bacillus subtilis*), *Pseudomonas* (e.g., *Pseudomonas putida, Pseudomonas chlororaphis*), *Pyrococcus* (e.g., *Pyrococcus abyssi*), *Comomonas* (e.g., *Comomonas testosterone*), and *Corynebacterium* (e.g., *Corynebacterium propinquum*) (see, e.g., Prasad, Biotechnology Advances (2010), 28(6): 725-741). The enzyme nitrile hydratase is either iron or cobalt-dependent (i.e. it possesses either an iron or a cobalt atom coordinated in its activity center) which is particularly characterized by its ability to catalyze conversion of acrylonitrile to obtain acrylamide by hydrating acrylonitrile (Kobayashi, Nature Biotechnology (1998), 16: 733-736). The capability of microorganisms to act as biocatalysts for converting acrylonitrile to acrylamide is basically dependent on two parameters: Sufficient growth of the microorganisms and their production rate of nitrile hydratase.

Many processes for removing the biocatalyst from the acrylamide solution after completion of the conversion of acrylonitrile to acrylamide are known in the state of the art, mainly applied in order to remove impurities from the reaction solution. It is generally accepted, that even small quantities of impurities can affect the polymerization of acrylamide monomers or prevent polymerization taking place at all. WO02/088372 describes e.g. a method and device for separating the biocatalyst from the acrylamide solution using a tube centrifuge or an annular gap centrifuge optionally in combination with flocculation. The biocatalyst is washed with water to remove residual monomer and then used in the next bioconversion reaction.

Alternatively, immobilized biocatalyst are used for acrylamide production as described e.g. in U.S. Pat. No. 4,248,968, WO2013188844 and TW411350 with the objectives of preventing elution of impurities from the biocatalyst, improving separability of the biocatalyst from the reaction product, and improving applicability of the biocatalyst to repeated use.

Removal of the biocatalyst after completion of the conversion of acrylonitrile to acrylamide can also be carried out by diverse filtration techniques, as described e.g. in EP2019146 and CN203319905, each with the target to remove impurities from the reaction solution.

However, presence of biocatalysts in the acrylamide solution also seems to be desirable, as reported by EP2264003 and US2011006258 where microbial cells having nitrile hydratase activity are exclusively added for stabilizing the aqueous acrylamide solution. Moreover, as disclosed in WO2005/054488, it is also intended that the biocatalyst is substantially not removed from the aqueous acrylamide solution after completion of the conversion of acrylonitrile to acrylamide. The document rather describes a process for preparing a polymer solution, wherein the monomer contains cellular material and/or components of the fermentation broth. Such polymers seem to have even specifically designed features and properties, without the need for removing either the biocatalyst or the fermentation broth.

Although a variety of methods describing the production of polyacrylamide solutions are known in the art, the use of polyacrylamides in tertiary oil recovery allows for further improvements. For example, rock layer injectability of the aqueous polyacrylamide solution is of particular relevance when introducing the polymer solution into the ground. More precisely, when using the biological synthesis method for acrylamide preparation, is should be avoided that cells of the biocatalyst having a size of similar magnitude as the rock pores get inside the polymerization mixture. However, separating the biocatalyst after polymerization is economically not possible.

In sum, there is a need in the art to provide new means and methods for producing polyacrylamide solutions with improved properties and high performance quality for use in the tertiary oil recovery, in order to further increase the mobility of the oil and raise the recovery rate from the reservoir's oil. The technical problem underlying the present application is thus to comply with this need. The technical problem is solved by providing the embodiments reflected in the claims, described in the description and illustrated in the examples and figures that follow.

SUMMARY OF THE INVENTION

The present invention is, at least partly, based on the surprising finding that separating a biocatalyst from a biocatalytically prepared aqueous acrylamide solution, such that the $OD_{600}$ of the aqueous acrylamide solution is equal to or less than 0.6, preferably equal to or less than 0.4, more preferably equal to or less than 0.3, even more preferably equal to or less than 0.2, still more preferably equal to or less than 0.15, still more preferably equal to or less than 0.12, still more preferably equal to or less than 0.1, still more preferably equal to or less than 0.075, most preferably equal to or less than 0.05, and subsequently polymerizing the aqueous acrylamide solution to polyacrylamide, provides a polyacrylamide solution having an increased viscosity. In particular, the viscosity of said polyacrylamide solution is increased when compared to a reference solution, wherein the reference solution is a polyacrylamide solution prepared from an aqueous acrylamide solution having an $OD_{600}$ of more than 0.6 and wherein the reference solution is prepared by the same method without separating the biocatalyst.

The value $OD_{600}$ indicates the absorbance, or optical density, of a liquid sample measured at a wavelength of 600 nm. It is a preferred method for determining the concentration or amount of a biocatalyst as described herein in an aqueous solution, such as an aqueous acrylamide solution. Accordingly, the $OD_{600}$ of an aqueous solution is measured, thereby the amount or concentration of a biocatalyst is determined.

Thus, the viscosity of the polyacrylamide solution prepared by the method of the present invention may depend on the residual amount of biocatalyst remaining in the aqueous acrylamide solution. This was unforeseeable, as it was not reported so far that the amount of remaining biocatalyst after bioconversion may directly influence the viscosity value of a polyacrylamide solution. The residual amount of biocatalyst may be determined by measuring the $OD_{600}$ of the aqueous acrylamide solution.

An aqueous acrylamide solution having an $OD_{600}$ which is equal to or less than 0.6 can for example be achieved by disc step separation performed with a low feed flow rate.

In some embodiments, the separation of the biocatalyst from the aqueous acrylamide solution is performed by centrifugation. Preferably the centrifugation is carried out by a disc stack separator.

In specific embodiments the centrifugation is performed with a feed flow rate of less than 600 l/h, preferably less than 500 l/h, more preferably less than 400 l/h, even more preferably less than 300 l/h, still more preferably less than 200 l/h or 100 l/h.

The separation of the biocatalysator from the acrylamid solution may be performed by filtration with a low feed flow rate. This may result in a polyacrylamid solution having a high viscosity. Further the filterability according to API RP 63 of the resulting polyacrylamide solution may be improved.

Thus another aspect of the invention refers to a method for producing a polyacrylamide solution having increased viscosity when compared to a reference solution, comprising the following steps:
  (a) preparing an aqueous acrylamide solution by converting acrylonitrile to acrylamide using a biocatalyst,
  (b) separating the biocatalyst from the aqueous acrylamide solution of step (a) by disc stack separation performed with a feed flow rate of less than 600 l/h,
  (c) polymerizing the aqueous acrylamide solution obtained in step (b) to polyacrylamide, wherein the reference solution is prepared by the same method without separating the biocatalyst.

The present invention is also directed to a method for increasing the viscosity of a polyacrylamide solution prepared by biocatalyzed conversion of acrylonitrile to acrylamide comprising the following steps:
  (a) preparing an aqueous acrylamide solution by converting acrylonitrile to acrylamide using a biocatalyst,
  (b) separating the biocatalyst from the aqueous acrylamide solution after completion of the conversion of acrylonitrile to acrylamide, such that the $OD_{600}$ of the aqueous acrylamide solution is equal to or less than 0.6, preferably equal to or less than 0.4, more preferably equal to or less than 0.3, even more preferably equal to or less than 0.2, still more preferably equal to or less than 0.15, still more preferably equal to or less than 0.12, still more preferably equal to or less than 0.1, still more preferably equal to or less than 0.075, most preferably equal to or less than 0.05,
  (c) polymerizing the aqueous acrylamide solution obtained in step (b) to polyacrylamide.

As disclosed herein, the viscosity of the polyacrylamide solution can be influenced using separation techniques which selectively separate the biocatalyst from the aqueous acrylamide solution, and leading to an $OD_{600}$ of the aqueous acrylamide solution equal to or less than 0.6.

Together the data of the present invention suggest for the first time, that separation of the biocatalyst from an aqueous acrylamide solution should preferably result in an acrylamide solution having an $OD_{600}$ equal to or less than 0.6, preferably equal to or less than 0.4, more preferably equal to or less than 0.4, even more preferably equal to or less than 0.3, still more preferably equal to or less than 0.2, still more preferably equal to or less than 0.1, most preferably equal to or less than 0.05 in order to obtain a polyacrylamide solution with increased viscosity as compared to a reference solution, wherein the viscosity values is >60 mPas at room temperature in artificial seawater. This was not expected, as it was never mentioned in the state of the art that separating the biocatalyst from an aqueous acrylamide solution prior to polymerization leads to an increased viscosity of the resulting polyacrylamide solution.

The present invention contributes to the state of the art with the finding that separating the biocatalyst from an aqueous acrylamide solution such that the $OD_{600}$ of the aqueous acrylamide solution is in the range of 0.6 to 0.001, such as equal to or less than 0.6, preferably equal to or less than 0.5, more preferably equal to or less than 0.4, even more preferably equal to or less than 0.3, still preferably equal to or less than 0.2, still more preferably equal to or less than 0.1, most preferably equal to or less than 0.05, but more than 0.025 or more; 0.01 or more; 0.005 or more; or 0.001 or more, leads to a polyacrylamide solution having an increased viscosity of 60 mPas or higher at room temperature in artificial seawater when compared to a reference solution. In the alternative or in addition to the lower border of $OD_{600}$ when referred to herein (i.e., but more than 0.025 or more; 0.01 or more; 0.005 or more; or 0.001 or more) it is envisaged that the aqueous acrylamide solution does not contain immobilized biocatalyst.

Although various separation techniques were known in the art, the direct interaction between the residual amount of biocatalyst in the aqueous acrylamide solution and the viscosity values of the resulting polyacrylamide solution has never been reported so far. Surprisingly the inventors have found that an acrylamide solution with a low residual amount of biocatalyst results in a polyacrylamide solution having an increased viscosity. Further, for the first time it is shown that an acrylamide solution having an $OD_{600}$ which is less than 0.6 results in a polyacrylamide solution having an increased viscosity. There is a demand for a method for producing a polyacrylamide solution having increased viscosity, because the application of polyacrylamide solutions in tertiary oil recovery specially counts on polymer solutions having high viscosity values accompanied by a reduced solubility, which is important in order to enhance the extraction outcome of the reservoir's oil from deeper rock layers. Thus, the inventors of the present application established a method for crucially improving the quality of a polyacrylamide solution.

In a first aspect, the present invention relates to a method for producing a polyacrylamide solution having increased viscosity when compared to a reference solution, comprising the following steps:
(a) preparing an aqueous acrylamide solution by converting acrylonitrile to acrylamide using a biocatalyst,
(b) separating the biocatalyst from the aqueous acrylamide solution after completion of the conversion of acrylonitrile to acrylamide, such that the $OD_{600}$ of the aqueous acrylamide solution is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05,
(c) polymerizing the aqueous acrylamide solution obtained in step (b) to polyacrylamide.

The present invention is also directed to a method for increasing the viscosity of a polyacrylamide solution prepared by biocatalyzed conversion of acrylonitrile to acrylamide comprising the following steps:
(a) preparing an aqueous acrylamide solution by converting acrylonitrile to acrylamide using a biocatalyst,
(b) separating the biocatalyst from the aqueous acrylamide solution after completion of the conversion of acrylonitrile to acrylamide, such that the $OD_{600}$ of the aqueous acrylamide solution is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05,
(c) polymerizing the aqueous acrylamide solution obtained in step (b) to polyacrylamide.

Accordingly, the present invention refers to a method for producing a polyacrylamide solution having increased viscosity when compared to a reference solution, comprising the following steps:

(a) preparing an aqueous acrylamide solution by converting acrylonitrile to acrylamide using a biocatalyst,
(b) separating the biocatalyst from the aqueous acrylamide solution of step (a) such that the $OD_{600}$ of the aqueous acrylamide solution is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05,
(c) polymerizing the aqueous acrylamide solution obtained in step (b) to polyacrylamide,
wherein the reference solution is a polyacrylamide solution prepared from an aqueous acrylamide solution having an $OD_{600}$ of more than 0.6 and wherein the reference solution is prepared by the same method without separating the biocatalyst.

Further, the present invention refers to a method for preparing a polyacrylamide solution prepared by biocatalyzed conversion of acrylonitrile to acrylamide comprising the following steps:
(a) preparing an aqueous acrylamide solution by converting acrylonitrile to acrylamide using a biocatalyst,
(b) separating the biocatalyst from the aqueous acrylamide solution of step (a) by disc stack separation performed with a specific settling area of 19.6 $m^2h/l$ or more,
(c) polymerizing the aqueous acrylamide solution obtained in step (b) to polyacrylamide.

In a preferred embodiment, the OD is measured directly after separating the biocatalyst.

In some embodiments of the present invention, any of the methods described herein further comprises at least one of the following steps:
(d) drying the polyacrylamide;
(e) shredding and/or squelching the polyacrylamide; and/or
(f) dissolving the polyacrylamide in an aqueous solution.

According to the present invention, the reference solution is a polyacrylamide solution prepared from an aqueous acrylamide solution having an $OD_{600}$ of more than 0.6, produced by any of the methods described herein without separating the biocatalyst.

Further, the viscosity of the polyacrylamide solution of the present invention is preferably more than 60 mPas at room temperature. In a preferred embodiment the viscosity of the polyacrylamide solution is more than 62 mPas at room temperature. In an even more preferred embodiment the viscosity of the polyacrylamide solution is more than 65 mPas at room temperature. In some embodiments of the present invention, the polyacrylamide is dissolved in artificial seawater. In some embodiments of the present invention, the polyacrylamide is dissolved in natural seawater.

Preferably, the separation of the biocatalyst is started within 5 h, preferably 2 h, more preferably 1 h, most preferably 30 minutes after completion of the conversation of acrylonitrile to acrylamide. In a more preferred embodiment the separation is started within 20 minutes hours after completion of the conversation of acrylonitrile to acrylamide. In an even more preferred embodiment the separation is started within 10 minutes after completion of the conversation of acrylonitrile to acrylamide.

In some embodiments of the present invention, the separation of the biocatalyst is performed by a disc stack separator. In some embodiments the separation of the biocatalyst is performed by a disk stack separator with a feed flow rate of less than 600 l/h, with feed flow rate of less than 500 l/h, with a feed flow rate of less than 400 l/h, with a feed flow rate of less than 300 l/h or with a feed flow rate of less than 200 l/h or 100 l/h.

Specific settling area values are preferred in the context of the present invention, in particular in the separation step of means, such as a product or composition, methods or uses of the present invention. Accordingly, it is a preferred embodiment of the means, methods and uses of the present invention that the separation of the biocatalyst is performed such that the specific settling area is 19.67 m²h/l or more, preferably of 23.6 m²h/l or more, more preferably 29.5 m²h/l or more, even more preferably 39.3 m²h/l or more, still more preferably 59.0 m²h/l or more, most preferably 118.0 m²h/l or more. Preferably, if the separation is performed such that the specific settling area is 19.67 m²h/l or more, preferably of 23.6 m²h/l or more, more preferably 29.5 m²h/l or more, even more preferably 39.3 m²h/l or more, still more preferably 59.0 m²h/l or more, or most preferably 118.0 m²h/l or more, the viscosity of a polyacrylamide solution will be increased when compared to a reference solution (not subjected to such a separation step). Hence, the separation step of a method or use of the present invention is preferably performed as follows: separating the biocatalyst from the aqueous acrylamide solution after completion of the conversion of acrylonitrile to acrylamide by filtration such that the specific settling area is 19.67 m²h/l or more, preferably of 23.6 m²h/l or more, more preferably 29.5 m²h/l or more, even more preferably 39.3 m²h/l or more, still more preferably 59.0 m²h/l or more, or most preferably 118.0 m²h/l or more. Specific settling area values may then be set in relation to $OD_{600}$ values (after separation). Thus, as explained above, $OD_{600}$ values referred to herein may correspond to specific settling area values. Hence, it is envisaged $OD_{600}$ values may also be replaced by specific settling area values.

Thus another aspect of the invention refers to a method for producing a polyacrylamide solution having increased viscosity when compared to a reference solution, comprising the following steps:
(a) preparing an aqueous acrylamide solution by converting acrylonitrile to acrylamide using a biocatalyst,
(b) separating the biocatalyst from the aqueous acrylamide solution of step (a) by disc stack separation performed with a feed flow rate of less than 600 l/h, preferably less than 500 l/h, more preferably less than 400 l/h, even more preferably less than 300 l/h, still more preferably less than 200 l/h or 100 l/h.
(c) polymerizing the aqueous acrylamide solution obtained in step (b) to polyacrylamide,
    wherein the reference solution is prepared by the same method without separating the biocatalyst.

In some embodiments of the method described herein the biocatalyst is flocculated prior to separation.

In some embodiments of the present invention the separation of the biocatalyst is performed by filtration. In some embodiments the filtration method is pressure filtration, such as for example, deep bed filtration or cake-forming filtration. In some embodiments the filtration method is precoat filtration. In some embodiments the filtration method is membrane filtration.

In some embodiments the separation of the biocatalyst is performed by immobilization. In some embodiments the immobilization technique is covalent binding to a surface. In some embodiments the immobilization technique is cross-linking. In some embodiments the immobilization technique is membrane separation. In some embodiments the immobilization technique is entrapment.

In some embodiments the aqueous acrylamide solution after separation of the biocatalyst in step (b) has an $OD_{600}$ of 0.01 or more, of 0.02 or more, of 0.03 or more.

In some embodiments of the present invention, the biocatalyst is a biocatalyst having nitrile hydratase activity. According to the present invention, the biocatalyst having nitrile hydratase activity is one selected from the group consisting of microorganisms belonging to *Rhodococcus, Aspergillus, Acidovorax, Agrobacterium, Bacillus, Bradyrhizobium, Burkholderia, Klebsiella, Mesorhizobium, Moraxella, Pantoea, Pseudomonas, Rhizobium, Rhodopseudomonas, Serratia, Amycolatopsis, Arthrobacter, Brevibacterium, Corynebacterium, Microbacterium, Micrococcus, Nocardia, Pseudonocardia, Trichoderma, Myrothecium, Aureobasidium, Candida, Cryptococcus, Debaryomyces, Geotrichum, Hanseniaspora, Kluyveromyces, Pichia, Rhodotorula, Escherichia, Geobacillus, Comomonas*, and *Pyrococcus*, and transformed microbial cells in which a nitrile hydratase gene is introduced. In preferred embodiments of the invention the biocatalyst is selected from bacteria of the genus *Rhodococcus, Pseudomonas, Escherichia* and *Geobacillus*.

In some embodiments the biocatalyst is *Rhodococcus erythropolis*. In some embodiments the biocatalyst is *Rhodococcus equi*. In some embodiments the biocatalyst is *Rhodococcus ruber*. In some embodiments the biocatalyst is *Rhodococcus opacus*. In some embodiments the biocatalyst is *Rhodococcus pyridinovorans*. In some embodiments the biocatalyst is *Aspergillus niger*. In some embodiments the biocatalyst is *Acidovorax avenae*. In some embodiments the biocatalyst is *Acidovorax facilis*. In some embodiments the biocatalyst is *Agrobacterium tumefaciens*. In some embodiments the biocatalyst is *Agrobacterium radiobacter*. In some embodiments the biocatalyst is *Bacillus subtilis*. In some embodiments the biocatalyst is *Bacillus pallidus*. In some embodiments the biocatalyst is *Bacillus smithii*. In some embodiments the biocatalyst is *Bacillus* sp BR449. In some embodiments the biocatalyst is *Bradyrhizobium oligotrophicum*. In some embodiments the biocatalyst is *Bradyrhizobium diazoefficiens*. In some embodiments the biocatalyst is *Bradyrhizobium japonicum*. In some embodiments the biocatalyst is *Burkholderia cenocepacia*. In some embodiments the biocatalyst is *Burkholderia gladioli*. In some embodiments the biocatalyst is *Klebsiella oxytoca*. In some embodiments the biocatalyst is *Klebsiella pneumonia*. In some embodiments the biocatalyst is *Klebsiella variicola*. In some embodiments the biocatalyst is *Mesorhizobium cicero*. In some embodiments the biocatalyst is *Mesorhizobium opportunistum*. In some embodiments the biocatalyst is *Mesorhizobium* sp F28. In some embodiments the biocatalyst is *Moraxella*. In some embodiments the biocatalyst is *Pantoea endophytica*. In some embodiments the biocatalyst is *Pantoea agglomerans*. In some embodiments the biocatalyst is *Pseudomonas chlororaphis*. In some embodiments the biocatalyst is *Pseudomonas putida*. In some embodiments the biocatalyst is *Rhizobium*. In some embodiments the biocatalyst is *Rhodopseudomonas palustris*. In some embodiments the biocatalyst is *Serratia liquefaciens*. In some embodiments the biocatalyst is *Serratia marcescens*. In some embodiments the biocatalyst is *Amycolatopsis*. In some embodiments the biocatalyst is *Arthrobacter*. In some embodiments the biocatalyst is *Brevibacterium* sp CH1. In some embodiments the biocatalyst is *Brevibacterium* sp CH2. In some embodiments the biocatalyst is *Brevibacterium* sp R312. In some embodiments the biocatalyst is *Brevibacterium* imperial. In some embodiments the biocatalyst is *Corynebacterium nitrilophilus*. In some embodiments the biocatalyst is *Corynebacterium pseudodiphteriticum*. In some embodiments the biocatalyst is *Corynebacterium glutamicum*. In some embodiments the biocatalyst is *Corynebacterium hoffmanii*. In some embodiments the biocatalyst is *Microbacterium imperial*. In some embodiments the biocatalyst is *Microbacterium smegmatis*. In some embodiments the biocatalyst is *Micrococcus luteus*. In some embodiments the biocatalyst is *Nocardia globerula*. In some embodiments the biocatalyst is *Nocardia rhodochrous*. In some embodiments the biocatalyst is *Pseudonocardia thermophile*. In some embodiments the biocatalyst is *Trichoderma*. In some embodiments the biocatalyst is *Myrothecium verrucaria*. In some embodiments the biocatalyst is *Aureobasidium pullulans*. In some embodiments the biocatalyst is *Candida famata*. In some embodiments the biocatalyst is *Candida guilliermondii*. In some embodiments the biocatalyst is *Candida tropicalis*. In some embodiments the biocatalyst is *Cryptococcus flavus*. In some embodiments the biocatalyst is *Cryptococcus* sp UFMG-Y28. In some embodiments the biocatalyst is *Debaryomyces hanseii*. In some embodiments the biocatalyst is *Geotrichum candidum*. In some embodiments the biocatalyst is *Geotrichum* sp JR1. In some embodiments the biocatalyst is *Hanseniaspora*. In some embodiments the biocatalyst is *Kluyveromyces thermotolerans*. In some embodiments the biocatalyst is *Pichia kluyveri*. In some embodiments the biocatalyst is *Rhodotorula glutinis*. In some embodiments the biocatalyst is *Escherichia coli*. In some embodiments the biocatalyst is *Geobacillus* sp. RAPc8. In some embodiments the biocatalyst is *Comomonas testosterone*. In some embodiments the biocatalyst is *Pyrococcus abyssi*. In some embodiments the biocatalyst is *Pyrococcus furiosus*. In some embodiments the biocatalyst is *Pyrococcus horikoshii*.

In a preferred embodiment of the present invention the biocatalyst is *Rhodococcus rhodochrous*. In some embodiments of the present invention the biocatalyst is of the strain *Rhodococcus rhodochrous* NCIMB 41164. In some embodiments of the present invention the biocatalyst is of the strain *Rhodococcus rhodocrous* J-1 (Accession number: FERM BP-1478). In some embodiments the biocatalyst is of the stain *Rhodococcus rhodocrous* M8 (Accession number: VKPMB-S926). In some embodiments of the present invention the biocatalyst is of the strain *Rhododcoccus rhodochrous* M33. In some embodiments the biocatalyst is of the strain *Escherichia coli* MT-10822 (Accession number: FERM BP-5785).

In another preferred embodiments of the present invention, the biocatalyst is *Rhodococcus pyridinovorans*.

In some embodiments the biocatalyst used herein has been dried before preparing the aqueous acrylamide solution. In some embodiments the drying method is freeze-drying. In some embodiments the drying method is spray drying. In some embodiments the drying method is heat drying. In some embodiments the drying method is air drying. In some embodiments the drying method is vacuum drying. In some embodiments the drying method is fluidized-bed drying. In some embodiments the drying method is spray granulation.

Another aspect of the present invention provides the use of an aqueous acrylamide solution having an $OD_{600}$ equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05 for the manufacture of a polyacrylamide solution having increased viscosity, wherein the biocatalyst is separated from the aqueous acrylamide solution prior to polymerization. The aqueous acrylamide solution is essentially produced by converting acrylonitrile to acrylamide using a biocatalyst. After separation the solution has preferably an $OD_{600}$ of 0.01 or more, such as 0.02 or more. In some embodiments the solution has an $OD_{600}$ of 0.01 or more.

In a further aspect, the present invention relates to an aqueous acrylamide solution having an $OD_{600}$ in the range of 0.6 to 0.001, such as having an $OD_{600}$ equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05, but having an $OD_{600}$ of 0.025 or more; of 0.01 or more; of 0.005 or more; or of 0.001 or more, wherein the aqueous acrylamide solution is produced by converting acrylonitrile to acrylamide using a biocatalyst and separating said biocatalyst from the aqueous acrylamide solution after completion of the conversation of acrylonitrile to acrylamide.

Another aspect of the present invention provides a polyacrylamide solution produced by any of the methods described herein.

In a further aspect, the present invention discloses a polyacrylamide having a viscosity of at least 60 mPas at room temperature in artificial sea water and produced by the polymerization of an aqueous acrylamide solution having an $OD_{600}$ equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05, but having an $OD_{600}$ of 0.025 or more; of 0.01 or more; of 0.005 or more; or of 0.001 or more, wherein the aqueous acrylamide solution is produced by converting acrylonitrile to acrylamide using a biocatalyst and separating said biocatalyst from the aqueous acrylamide solution after completion of the conversation of acrylonitrile to acrylamide.

Another aspect of the present invention relates to a method for producing a polyacrylamide solution having a viscosity of more than 60 mPas at room temperature, comprising the following steps:
(a) preparing an aqueous acrylamide solution by converting acrylonitrile to acrylamide using a biocatalyst,
(b) separating the biocatalyst from the aqueous acrylamide solution after completion of the conversion of acrylonitrile to acrylamide, such that the $OD_{600}$ of the aqueous acrylamide solution is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05,
(c) polymerizing the aqueous acrylamide solution obtained in step (b) to polyacrylamide.

Moreover, the invention refers to a method for producing an acrylamide solution comprising the following steps:
(a) preparing an aqueous acrylamide solution by converting acrylonitrile to acrylamide using a biocatalyst,
(b) separating the biocatalyst from the aqueous acrylamide solution of step (a) such that the $OD_{600}$ of the aqueous acrylamide solution is equal to or less than 0.6.

Further, the invention refers to the use of an aqueous acrylamide solution having an $OD_{600}$ equal to or less than 0.6, for increasing the viscosity of a polyacrylamide solution prepared from said acrylamide solution.

DETAILED DESCRIPTION OF THE INVENTION

The following description includes information that may be useful in understanding the present invention. It is not an admission that any of the information provided herein is prior art or relevant to the presently claimed inventions, or that any publication specifically or implicitly referenced is prior art.

It is to be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Those skilled in the art will recognize, or be able to ascertain, using not more than routine experimentation, many equivalents to the specific embodiments of the invention described herein. Such equivalents are intended to be encompassed by the present invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the methods and uses described herein. Such equivalents are intended to be encompassed by the present invention.

Several documents are cited throughout the text of this disclosure. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to 2%, up to 1%, or up to 0.5% above or below that value. In one embodiment "about" refers to a range up to 0.1% above and below a given value.

As stated above, the present invention discloses for the first time that separating a biocatalyst from a biocatalytically prepared aqueous acrylamide solution, such that the $OD_{600}$ of the aqueous acrylamide solution is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05, but having an $OD_{600}$ of 0.025 or more; of 0.01 or more; of 0.005 or more; or of 0.001 or more and subsequently polymerizing the aqueous acrylamide solution to polyacrylamide, results in a polyacrylamide solution having an increased viscosity when compared to a reference solution, wherein the reference solution is a polyacrylamide solution prepared from an aqueous acrylamide solution having an $OD_{600}$ of more than 0.6 and wherein the reference solution is prepared by the same method without separating the biocatalyst.

Although there was no indication in the state of the art, the inventors of the present invention surprisingly found that there is a direct correlation between the residual amount of biocatalyst remaining the acrylamide solution and the viscosity of the resulting polyacrylamide solution. These findings were unforeseeable, as although a wide variety of separation methods are described in the state of the art, a direct influence of the amount of a biocatalyst in an aqueous acrylamide solution on the viscosity of the resulting polyacrylamide solution has not been reported previously. Accordingly, the methods described herein allow for the production of a polyacrylamide solution having increased viscosity and higher quality, which can be further applied in tertiary oil recovery.

The present invention provides, amongst others, a method for producing a polyacrylamide solution having increased viscosity when compared to a reference solution, comprising the following steps:
(a) preparing an aqueous acrylamide solution by converting acrylonitrile to acrylamide using a biocatalyst,
(b) separating the biocatalyst from the aqueous acrylamide solution after completion of the conversion of acrylonitrile to acrylamide, such that the $OD_{600}$ of the aqueous acrylamide solution is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05, (c) polymerizing the aqueous acrylamide solution obtained in step (b) to polyacrylamide.

In particular, the present invention refers to a method for producing a polyacrylamide solution having increased viscosity when compared to a reference solution, comprising the following steps:

(a) preparing an aqueous acrylamide solution by converting acrylonitrile to acrylamide using a biocatalyst, (b) separating the biocatalyst from the aqueous acrylamide solution of step (a) such that the $OD_{600}$ of the aqueous acrylamide solution is equal to or less than 0.6, (c) polymerizing the aqueous acrylamide solution obtained in step (b) to polyacrylamide, wherein the reference solution is a polyacrylamide solution prepared from an aqueous acrylamide solution having an $OD_{600}$ of more than 0.6 and wherein the reference solution is prepared by the same method without separating the biocatalyst.

The term "increased viscosity" or "increasing viscosity" when used in any of the aspects of the present invention in the context of a polyacrylamide solution refers to a significant higher viscosity value of said polyacrylamide solution when compared to a reference solution. Viscosity is generally a measure of the resistance of a fluid, and the more viscous the fluid is, the lesser its ease of movement. Thus, the term "increased viscosity" when used herein means that the polyacrylamide solution is thicker and thus less easy to move when compared to a reference solution. According to the present invention, the viscosity of the polyacrylamide solution prepared from an aqueous acrylamide solution having an $OD_{600}$ equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05 is at least 10% higher than the viscosity value of the reference solution. Preferably, the viscosity of the polyacrylamide solution prepared from an aqueous acrylamide solution having an $OD_{600}$ equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05 is at least 15% higher than the viscosity value of the reference solution. Most preferably, the viscosity of the polyacrylamide solution prepared from an aqueous acrylamide solution having an $OD_{600}$ equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05 is at least 20% higher than the viscosity value of the reference solution.

When measuring the viscosity of the polyacrylamide solution prepared by any of the methods described herein, the polyacrylamide prepared is dissolved in artificial seawater. In some embodiments the polyacrylamide solution prepared by any of the methods provided herein is dissolved in natural seawater. According to the present invention, it is envisaged that the viscosity of the polyacrylamide solution is determined by any conventional method using any kind of viscometer, such a capillary viscometer, rotational viscometer, a viscosity beaker, falling weight viscometer, process viscometer, quartz viscometer and the like, preferably at room temperature (19-26° C.), more preferably at 25° C.+/− 1° C. The viscosity can be measured by a rheomether. Preferably the viscosity is measured at a shear rate of 7 1/s at room temperature at a rheometer with DIN double gap geometry.

The term "artificial sea water" refers to a solution prepared by the standard ASTM D1141-98, i.e. NaCl 24.53 g/l, MgCl2 5.20 g/l, Na2SO4 4.09 g/l, CaCl2 1.16 g/l, KCl 0.695 g/l, NaHCO3 0.201 g/l, KBr 0.101 g/l, H3BO3 0.027 g/l, SrCl2 0.025 g/l, NaF 0.003 g/l.

According to the present invention, the reference solution is a polyacrylamide solution prepared from an aqueous acrylamide solution having an $OD_{600}$ of more than 0.6 and wherein the reference solution is prepared by the same method without separating the biocatalyst. In a preferred embodiment the reference solution is an aqueous acrylamide solution prepared by any of the methods of the present invention without separating the biocatalyst from the aqueous acrylamide solution after completion of the conversion of acrylonitrile to acrylamide prior to polymerization. Thus, the reference solution is generally prepared by the methods of the present invention without performing the separation step (b).

The viscosity of the polyacrylamide solution of the present invention is essentially more than 60 mPas at room temperature. Preferably, the viscosity of the polyacrylamide solution prepared by the methods of the present invention is more than 62 mPas at room temperature. Most preferably, the viscosity of the polyacrylamide solution prepared by the methods of the present invention is more than 65 mPas at room temperature.

In a measurement of $OD_{600}$ of an aqueous acrylamide solution as described herein the following preferred reference value may be used: the $OD_{600}$ of a saturated solution of acrylamide in water, or demineralized water. Alternatively, the reference value may be one which is measured after an aqueous solution, such as an aqueous acrylamide solution that contains the biocatalyst, is subjected to filtration, whereby the pore size of the filter may be 0.1 μm. For example, filtration may be performed with a filter having a pore of 0.4 μm, followed by filtration with a filter having a pore of 0.2 μm and subsequently followed by filtration with a filter having a pore of 0.1 μm. At a pore size of 0.2 μm or 0.1 μm it is envisaged that neither cells of the biocatalyst nor cell debris will pass the filter and, thus, the filtrate will essentially be free of the biocatalyst used. Hence, whenever $OD_{600}$ of an aqueous solution is measured herein, said reference value is preferably used in relation to an $OD_{600}$ value as described in the context of the means, methods and uses of the present invention. In the context of measuring $OD_{600}$ of a biocatalyst, the biocatalyst includes life cells, dead cells, and/or cell debris, such as cell walls, cell membranes, and organelles. Thus, when $OD_{600}$ of an aqueous solution including biocatalyst is measured herein, the measurement includes life cells, dead cells, cell debris and the like of a biocatalyst. $OD_{600}$ can, for example, be measured by photometry, such as UV/VIS-spectroscopy.

Accordingly, the present invention also provides a method for producing a polyacrylamide solution having a viscosity of more than 60 mPas at room temperature, comprising the following steps:

(a) preparing an aqueous acrylamide solution by converting acrylonitrile to acrylamide using a biocatalyst, (b) separating the biocatalyst from the aqueous acrylamide solution of step (a), such that the $OD_{600}$ of the aqueous acrylamide solution is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05, (c) polymerizing the aqueous acrylamide solution obtained in step (b) to polyacrylamide.

Preferably, the biocatalyst is separated from the aqueous acrylamide solution after completion the conversion of acrylonitrile to acrylamide.

The term "converting" or "conversion" when used in the context of the present invention refers to the total or partially reaction of the acrylonitrile reagent to the acrylamide product in aqueous solution using a biocatalyst. More precisely, "conversion" or "converting" means, that the acrylonitrile is allowed to undergo hydration reaction by the use of a biocatalyst in aqueous solution in order to obtain an acrylamide reaction solution having a desired concentration. According to the present invention, this hydration reaction may be carried out in any conventional manner. The concentration of the acrylonitrile is not specifically restricted provided that the acrylamide reaction solution of a desired concentration is obtained. Although the upper limit of the concentration of the acrylonitrile is not specifically restricted, feed of excess acrylonitrile needs a large catalytic amount for completion of the reaction, a reactor having an excess volume and an excess heat exchanger for removal of heat, so that the economic burden in the equipment aspect becomes heavy. In the case of acrylonitrile, it is preferable to feed acrylonitrile in such an amount that the theoretical produced solution concentration of acrylamide in the reaction solution of (a) in the reactor becomes 42 to 80 w/w % when all the acrylonitrile becomes the corresponding acrylamide. More specifically, it is preferable to feed acrylonitrile in an amount of 0.4 to 1.5 parts by weight based on 1 part by weight of the aqueous medium.

In context with any one of the methods of the present invention, the acrylonitrile may be added to the reactor before the water is added, after water is added, or added together with water. According to any one of the methods described herein, the acrylonitrile may be added continuously or intermittently. Addition of acrylonitrile may be at constant or variable feed rate or batch-wise. In addition, in any one of the methods described and provided herein, water is added to the reactor in step (a). The water may be added as such, be part of the biocatalyst as described herein, be part of an acrylonitrile solution as described herein, or otherwise be added. The microbial catalyst may be used in any amount provided that the acrylamide reaction solution (I) of a desired concentration is obtained, and the amount thereof is properly determined according to the reaction conditions, the type of the catalyst and the form thereof. However, the amount of the microbial catalyst is in the range of usually 10 to 50000 ppm by weight, preferably 50 to 30000 ppm by weight, in terms of weight of dry bacterial cell, based on the aqueous medium.

The reaction time of the hydration reaction is not specifically restricted either provided that the acrylamide reaction solution of a desired concentration is obtained. Although the reaction time depends upon the amount of the catalyst used and the conditions such as temperature, it is specifically in the range of usually 1 to 80 hours, preferably 2 to 40 hours, based on one reactor. Although the hydration reaction is usually carried out at atmospheric pressure, it may be carried out under pressure in order to increase solubility of the acrylonitrile in the aqueous medium. The reaction temperature is not specifically restricted provided that it is not lower than the ice point of the aqueous medium. However, it is desirable to carry out the reaction at a temperature of usually 0 to 50° C., preferably 10 to 40° C. The pH value of the aqueous medium in the hydration reaction is not specifically restricted and may be any value provided that the activity of nitrile hydratase is maintained. However, the pH value of the aqueous medium is desired to be in the range of preferably 6 to 10, more preferably 7 to 9. The hydration reaction may be carried out by any of a batch process and a continuous process, and the reaction may be carried out by selecting its reaction system from reaction systems such as suspended bed, a fixed bed, a fluidized bed and the like or by combining different reaction systems according to the form of the catalyst.

Through such hydration reaction, the acrylamide reaction solution of step (a) is obtained. In this reaction solution, acrylamide, the aqueous medium, the microbial catalyst dissolved are contained, and in addition, solid matters such as the microbial catalyst fixed onto a carrier and dead bacterial cells are sometimes contained. The concentration of acrylamide obtained in step (a) is in the range of usually 42 to 80 w/w %. The concentration of acrylamide in the reaction solution or the aqueous solution can be measured by a conventional method, such as high performance liquid chromatography, gas chromatography or a method of using a refractometer. Those skilled in the art are aware of numerous methods and conditions which will enable a practitioner to prepare an aqueous acrylamide solution by converting acrylonitrile to acrylamide using a biocatalyst.

According to the disclosure of the present invention, after completion of the conversion of the acrylonitrile to acrylamide, the biocatalyst is essentially separated from the aqueous acrylamide solution. The term "separated" does not necessarily denote a complete separation of the biocatalyst and/or its components from the aqueous acrylamide solution. Thus, the aqueous acrylamides solution may comprise residual parts of biocatalyst after separation. In some embodiments the biocatalyst and/or its components is partially removed. In some embodiments the biocatalyst and/or its components is completely removed. In the context of the present invention, the term "separating" can be also understood as the total or partially removal of the biocatalyst used for converting acrylonitrile to acrylamide from the biocatalytically prepared aqueous acrylamide solution, resulting in an $OD_{600}$ of the aqueous acrylamide solution of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05. In any of the embodiments disclosed herein, the word "separating" or "separation" can be equally replaced by the word "discharging" or "discharge". According to the present invention, preferably equal to or more than 80 w/w % of the biocatalyst based on the biocatalyst present in the aqueous acrylamide solution at the completion of the reaction is removed in such separation. More preferably, equal to or more than 90 w/w % of the biocatalyst based on the biocatalyst present in the aqueous acrylamide solution at the completion of the reaction is removed in such separation. Even more preferably, equal to or more than 95 w/w % of the biocatalyst based on the biocatalyst present in the aqueous acrylamide solution at the completion of the reaction is removed in such separation. Most preferably, equal to or more than 99 w/w % of the biocatalyst based on the biocatalyst present in the aqueous acrylamide solution at the completion of the reaction is removed in such separation. Accordingly, the residual amount of the biocatalyst in the aqueous acrylamide solution is equal to or less than 20 w/w % based on the biocatalyst present in the aqueous acrylamide solution at the completion of the reaction is removed in such separation. Preferably, the residual amount of the biocatalyst in the aqueous acrylamide solution is equal to or less than 10 w/w % based on the biocatalyst present in the aqueous acrylamide solution at the completion of the reaction. More preferred the residual amount of the biocatalyst in the aqueous acrylamide solution is equal to or less than 5 w/w % based on the biocatalyst present in the aqueous acrylamide solution at the completion of the reaction. Most preferred the residual amount of the biocatalyst in the aqueous acrylamide solution is equal to or less than 2 w/w %, preferably less than 1 w/w %, more preferably less than 0.5 w/w % based on the biocatalyst present in the aqueous acrylamide solution at the completion of the reaction. According to the present invention, in some embodiments the amount of the remaining biocatalyst is more than 0.5 w/w % based on the biocatalyst present in the aqueous acrylamide solution at the completion of the reaction.

As described herein above, according to the present invention the amount of biocatalyst in an aqueous acrylamide solution prior to polymerization is significantly reduced after separation of said biocatalyst by any of the separation techniques described herein elsewhere. Thus, in a further aspect the present invention also provides a method for reducing the amount of biocatalyst in a biocatalytically prepared aqueous acrylamide solution to a remaining amount of biocatalyst equal to or less than 20 w/w %, preferably less than 10 w/w % as based on the total weight of the biocatalyst in the aqueous acrylamide solution, the method comprising separating the biocatalyst from the aqueous acrylamide solution prior to polymerization, wherein a polyacrylamide solution prepared from the aqueous acrylamide solution having a remaining amount of biocatalyst equal to or less than 20 w/w %, preferably less than 10 w/w % based on the total weight of the biocatalyst in the aqueous acrylamide solution has an increased viscosity as compared to a reference solution.

In any one of the methods described and provided herein, the separation of the biocatalyst is started after completion of the conversion of acrylonitrile to acrylamide using a biocatalyst. The term "after completion" when used herein can be understood as the point of time when the desired acrylamide concentration in the aqueous solution according to the present invention is achieved. The term "after completion" may refer to the point of time when 99.99% of the total amount of acrylonitrile fed to the reaction mixture has been converted. In other the words the term "after completion" may refer to the point of time when the total amount of acrylonitrile fed to the reaction mixture has been converted so that the remaining acrylonitrile concentration is equal or less than 100 ppm, wherein ppm refers to weight parts based on the total weight of the aqueous acrylamide solution. The separation may be started immediately after completion of the conversion of acrylonitrile to acrylamide, or within a specific time interval. In a preferred embodiment of the present invention, the separation is started within 5 h, preferably 2 h, more preferably 1 h, most preferably 30 minutes after completion of the conversation of acrylonitrile to acrylamide. In a more preferred embodiment the separation is started within 20 minutes after completion of the conversation of acrylonitrile to acrylamide. In a most preferred embodiment the separation is started within 10 minutes after completion of the conversation of acrylonitrile to acrylamide.

The separation performance was specified by the remaining biomass in the aqueous acrylamide solution measured as Optical Density at 600 nm ($ODOD_{600}$). $OD_{600}$ measurements were performed using a Shimadzu Europe UV-1650PC double-beam spectrophotometer, and the samples were measured in 1 cm light path semi-micro PS cuvettes against a reference solution. Demin. water was used as reference sample. The results are shown in Tables 1 and 2, indicating that lower feed flow rates lead to small $OD_{600}$ values, indicating a minor amount of remaining biocatalysts in the aqueous acrylamide solution.

According to the present invention, an aqueous acrylamide having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05 can be used for the manufacture of a polyacrylamide solution having increased viscosity, wherein the biocatalyst is separated from the aqueous acrylamide solution prior to polymerization. In particular, the aqueous solution having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05 can be used for the manufacture of a polyacrylamide solution having a viscosity of more than 60 mPas. Preferably, the aqueous solution having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05 can be used for the manufacture of a polyacrylamide solution having a viscosity of more than 62 mPas. Most preferably, the aqueous solution having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05 can be used for the manufacture of a polyacrylamide solution having a viscosity of more than 65 mPas. The aqueous acrylamide solution having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05 used for the manufacture of a polyacrylamide solution as described herein is essentially prepared by converting acrylonitrile to acrylamide using a biocatalyst and separating said biocatalyst from the aqueous acrylamide solution after completion of the conversation of acrylonitrile to acrylamide. As disclosed herein, the remaining amount of biocatalyst in an aqueous acrylamide solution containing equal to or less than 20 w/w %, preferably less than 10 w/w % of biocatalyst as referred to the total weight of the aqueous acrylamide solution is after separation more than 0.015 w/w %, preferably 0.01 w/w % based on the total weight of the aqueous acrylamide solution. In some embodiments the remaining amount is <0.4 w/w %, preferably <0.1 w/w %, more preferably <0.05 w/w %, most preferably <0.025 w/w % based in the total amount of the aqueous acrylamide solution. The term "remaining amount" or "residual amount" when used herein refers to the amount of biocatalyst that is not separated from the aqueous acrylamide solution by any of the separation techniques described herein. According to the present invention, in some embodiments the separation step of (b) in any of the methods provided herein does not result in a complete discharge of the biocatalyst, but a part remains in the aqueous acrylamide solution.

The separation of the biocatalyst from the aqueous acrylamide solution can be performed by any of the techniques disclosed and described herein by reference. Preferably, separation of the biocatalyst can be performed by a disc stack separator. Using a disk stack separator, solids can be separated from liquids in a continuous process using extremely large centrifugal forces. With this force, the solids are pressed to the higher density against the inner wall of the rotating drum and the liquid phase with the lower density is collected in the center of the drum in phases. Appropriate disc stack separator models suitable to be used in any of the methods of the present invention are known to those skilled in the art.

In particular, the inventors have found that by using a disc stack separator for separating the biocatalyst from the aqueous acrylamide solution with a specific settling area of 19.67 m2h/l or more, the viscosity of the resulting polyacrylamide solution increases as compares to a reference solution depending on the speed of separation (Tables 1 and 2). The reference solution in the scope of the present invention is defined elsewhere herein. In particular, when using a disc stack separator for separating the biocatalyst from the aqueous acrylamide solution with a specific settling area of equal or more than 19.67 m2h/l, the viscosity of the resulting polyacrylamide solution was always equal to or more than 60 mPas, a specific settling area of equal or more than 29.5 m2h/l equal to or more than 62 mPas, and for a specific settling area of equal or more than 39.3 m2h/l equal to or more than 63 mPas as compared to a reference solution, respectively (Tables 1 and 2). Moreover, the inventors found that a specific settling area of equal or more than 23.6 m2h/l result in a better filterability of the polyacrylamide solution with "Millipore filtration rate"-values (MPFR-values) according to API RP 63 of less than 1.3 at a filter pore diameter of 3 µm and 5 µm. Moreover, the inventors found that a specific settling area of equal or more than 29.5 m2h/l result in a better filterability of the polyacrylamide solution with "Millipore filtration rate"-values (MPFR-values) according to API RP 63 of less than 1.3 at a filter pore diameter of 2 µm, 3 µm and 5 µm. Moreover, the inventors found that a specific settling area of equal or more than 39.3 m2h/l result in a better filterability of the polyacrylamide solution with "Millipore filtration rate"-values (MPFR-values) according to API RP 63 of less than 1.3 at a filter pore diameter of 1.2 µm, 2 µm, 3 µm and 5 µm (Tables 1 and 2). MPFR-values have been determined as described elsewhere herein.

The specific settling area may be less than 500 m2h/l, less than 400 m2h/l, less than 300 m2h/l, less than 200 m2h/l, or less than 150 m2h/l.

When using a disc stack separator for separating the biocatalyst from the aqueous acrylamide solution with a feed flow rate between 200 and 600 l/h, the viscosity of the resulting polyacrylamide solution may be equal to or more than 60 mPas, for a feed flow rate between 200 and 400 l/h equal to or more than 62 mPas, and for a feed flow rate between 200 and 300 l/h equal to or more than 63 mPas as compared to a reference solution, respectively (Tables 1 and 2). Moreover, the a feed flow rate between 200 and 500 l/h may result in a better filterability of the polyacrylamide solution with "Millipore filtration rate"-values (MPFR-values) according to API RP 63 of less than 1.3 at a filter pore diameter of 3 µm and 5 µm. Moreover, the a feed flow rate between 200 and 400 l/h may result in a better filterability of the polyacrylamide solution with "Millipore filtration rate"-values (MPFR-values) according to API RP 63 of less than 1.3 at a filter pore diameter of 2 µm, 3 µm and 5 µm. Moreover, a feed flow rate between 200 and 300 l/h may result in a better filterability of the polyacrylamide solution with "Millipore filtration rate"-values (MPFR-values) according to API RP 63 of less than 1.3 at a filter pore diameter of 1.2 µm, 2 µm, 3 µm and 5 µm (Tables 1 and 2). MPFR-values have been determined as described elsewhere herein.

Accordingly, in one aspect the present invention provides a polyacrylamide solution with increased viscosity and a better filterability as compared to a reference solution, obtainable by any of the methods described herein. In particular, separating the biocatalyst from the aqueous acrylamide solution after completion of the conversion of acrylonitrile to acrylamide, such that the $OD_{600}$ of the aqueous acrylamide solution is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05 may lead to a resulting polyacrylamide solution having an increased viscosity and a better filterability according to API RP 63 as compared to a reference solution. Filterability is the capability of a solution to pass a filter membrane having a defined pore diameter. The term "better filterability" when used herein refers to a solution that may easier pass a filter membrane having a defined pore diameter as compared to a reference solution. API RP 63 refers to the "Recommended Practices for Evaluation of Polymers Used in Enhanced Oil Recovery Operations". The filterability is measured as MPFR-(Millipore filtration rate)-value as described elsewhere herein. In some embodiments the filterability of the polyacrylamide solution of the present invention is less than 1.3 at a filter pore diameter of 1.2 µm, 2 µm, 3 µm and 5 µm. In a preferred embodiment the filterability of the polyacrylamide solution of the present invention is less than 1.2 at a filter pore diameter of 1.2 µm, 2 µm, 3 µm and 5 µm.

The separation conditions therefore directly influence the residual amount of the remaining biocatalyst, which is reflected in a better filterability and an increased viscosity of the resulting polyacrylamide solution. Thereby, slower feed flow rates are preferred, because of a higher discharge of biomass from the acrylamide solution. Moreover, it has surprisingly found that the remaining amount of biocatalyst in the aqueous acrylamide solution after separation does directly define and influence the viscosity of the resulting polyacrylamide solution, wherein the viscosity of the resulting polyacrylamide solution is higher when more biocatalyst is separated. Therefore, according to the present invention, the preferred feed flow rate when using a disk stack separator is less than 600 l/h. More preferred is a feed flow rate of less than 500 l/h. Even more preferred is a separator flow rate of less than 400 l/h. Still more preferred is a separator flow rate of less than 300 l/h. Most preferred is a separator flow rate of less than 200 l/h or 100l/h or less. The $OD_{600}$ after separation is equal to or less than 0.6, preferably equal to or less than 0.5, more preferably equal to or less than 0.4, even more preferably equal to or less than 0.3, still more preferably equal to or less than 0.2, still more preferably equal to or less than 0.1, most preferably equal to or less than 0.05.

The equivalent settling area or equivalent clarification surface is a parameter describing the centrifuge. The equivalent settling area may be for example 11800 m2.

The term "specific settling area" is a parameter describing the separation process. The specific settling area is defined as equivalent settling area of the disc stack centrifuge divided by the feed flow rate. This parameter is particular useful to describe the separation process.

Preferably, the $OD_{600}$ is measured directly after separating the biocatalyst from the aqueous acrylamide solution. This means that the $OD_{600}$ value is achieved by the separation of the biocatalyst and not by other measures such as dilution of the aqueous acrylamide solution.

In another embodiment of the present invention, the separation of the biocatalyst from the aqueous acrylamide solution can be performed by filtration. Appropriate filtration methods are described in the state of the art, e.g. in EP2019146 and CN203319905. Preferred filtration methods according to the present invention are selected from the group consisting of pressure filtration, precoat filtration, and membrane filtration. For pressure filtration, preferably layer filters and module filters can be used, wherein the biomass remains in a filter cake made from cellulose, whereas the liquid phase with the acrylamide product can pass this layer. When using precoat filtration, cartridge filters are often applied, wherein a layer of filter aids (e.g. cellulose) is accumulated before the actual filtration of the reaction suspension. Under such conditions, the biocatalyst remains partly on the precoat layer and partly inside the precoat layer. Another filtration method using a cross-flow film is described in detail in WO2004089518 and can be applied as well in any of the methods according to the present invention. The outcome of the filtration performance can be measured by determining the amount of residual biocatalyst in the aqueous acrylamide solution for example by measuring the OD of the reaction mixture as described herein.

In a particular embodiment of the present invention, the biocatalyst is flocculated prior to separation. Within the scope of the present invention, flocculation means that suspended or colloidal impurities of the aqueous solution, such as the biocatalyst as disclosed herein are coagulated in order to be better separated from water by sedimentation or filtration and to be removed. I some embodiments the flocculation can be carried out in the reactor where acrylonitrile is converted to acrylamide. Preferably the flocculation is carried out in a separate flocculation tank. According to the present invention, the flocculation can be performed using any of the flocculants known in the state of the art. Preferably the flocculant used herein is aluminium sulfate, aliminium chloride, polyaluminium chlorids, ferric sulfate, ferric chloride, polyelectrolyte and/or an anionic polymer such as Praestol® 2510 or Praestol® as described in WO02/088372 and DE19828467. Preferably the flocculation is carried out at a pH of 6.8 to 8.0. More preferably the flocculation is carried out at a pH of 7.0 to 7.5.

According to another embodiment of the present invention, the separation of the biocatalyst is performed by immobilization. Immobilization means, that the biocatalyst as used herein is spatially fixed in gel particles, capsules or in bounded reaction spaces, leading to a shift of the catalytic activity. Immobilized biocatalyst are used for a long in processes for producing acrylamide, having the advantage of an easier isolation, purification and regeneration of the immobilized biocatalyst after completion of the conversion of acrylonitrile to acrylamide. Commonly used immobilization techniques comprise covalent binding to a surface, crosslinking, membrane separation, and entrapment, which can all be applied in any of the aspects described in the present invention. As an example, biocatalyst can be immobilized on a polyacrylamide gel, alginate, carrageenan or ion exchange resin. In a particular embodiment of the present invention, the immobilized biocatalyst of the present invention is substantially irreversibly retained in the interior of an open, porous, highly hydrophilic polymer, wherein there is an essential absence of debris generation from metabolic activity of the microorganism during the metabolic bioconversion as described in WO2013188844. Also columns filled with immobilized biocatalysts having nitrile hydratase activity as disclosed in U.S. Pat. No. 4,248,968 can be used according to the present invention. In sum, immobilization of the biocatalyst of the present invention can be carried out in any conventional manner that the person skilled in the art knows.

Alternatively the biocatalyst of step a) is not immobilized.

In a further embodiment the biocatalyst of step a) is not immobilized and is also not immobilized in a further step before the separation step b).

For removing of solid matters such as biocatalyst from an aqueous acrylamide solution, further techniques such as centrifugation and film separation are described in the state of the art, e.g. in WO02/088372, which are also within the scope of the present invention. Preferred centrifuges used in any of the methods or uses of the present invention are self-draining centrifuges and annular gap centrifuges.

After separating the biocatalyst from the aqueous acrylamide solution after completion of the conversion of acrylonitrile to acrylamide, the aqueous acrylamide solution having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05, but more than 0.025 or more; 0.01 or more; 0.005 or more; or 0.001 or more, is polymerized to polyacrylamide. The resulting polyacrylamide has a viscosity of at least 60 mPas at room temperature in artificial sea water when produced by polymerization of an aqueous acrylamide solution having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05, but more than 0.025 or more; 0.01 or more; 0.005 or more; or 0.001 or more. The term "polymerzing" or "polymerized" as used herein refers to a process of reacting monomer molecules together in a chemical reaction to form polymer chains or three-dimensional networks. In the context of the present invention the term "polymerzing" or "polymerized" means that the aqueous acrylamide solution obtained by any of the methods described herein is converted into its homopolymer or copolymer. With respect to this, in case of a homopolymer the term "polymerizing" refers to a homopolymerization reaction, while in case of a copolymer the term "polymerizing" refers to a copolymerization reaction. Homopolymerization and copolymerization may be performed using an aqueous solution obtainable or being obtained by any of the methods described herein. According to the present invention, as an example the polymerization of the aqueous acrylamide solution having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05, but more than 0.025 or more; 0.01 or more; 0.005 or more; or 0.001 or more can be carried out as described in detail herein in the Examples. The obtained polyacrylamide can be further dried, shredded and/or squelched to a polyacrylamide and/or dissolved in aqueous solution as described in the Examples in order to obtain the aqueous polyacrylamide solution of the present invention. Further methods to dry, shred and/or squelch a polyacrylamide obtained from an aqueous acrylamide solution are known to those skilled in the art. The obtained polyacrylamide powdery polyacrylamide may be dissolved in any appropriate aqueous solution. Preferably, the polyacrylamide of the present invention is subsequently dissolved in artificial or natural seawater.

Accordingly, in some embodiments, the methods described and provided herein may further comprise at least one of the following steps:
(d) drying the polyacrylamide;
(e) shredding and/or squelching the polyacrylamide; and/or
(f) dissolving the polyacrylamide in an aqueous solution.

According to the present invention, the polyacrylamide solution having an increased viscosity as compared to a reference solution can be produced by any of the methods disclosed or described herein. In particular, the polyacrylamide solution of the present invention having a viscosity of 60 mPas or more at room temperature can be prepared by any of the methods disclosed or described herein.

The viscosity of the polyacrylamide solution is more than 60 mPas, preferably more than 65 mPas at room temperature when the polyacrylamide is dissolved at a concentration of 4000 ppm in artificial seawater, wherein ppm refers to weight parts based on the total weight of the polyacrylamide solution. Preferably, the viscosity of the polyacrylamide solution less than 200 mPas, preferably 150 mPas. In particular, the viscosity of the polyacrylamide solution is less than 200 mPas, preferably 150 mPas when the polyacrylamide is dissolved at a concentration of 4000 ppm in artificial seawater.

The terms "aqueous solution" or "aqueous medium" when used herein refer to an aqueous liquid for use in the present invention, in which a buffering agent such as phosphate, an inorganic salt such as sulfate or carbonate, a hydroxide of an alkali metal, an amide compound or the like is dissolved in an appropriate concentration. Into the aqueous solution or the aqueous medium, acrylonitrile and the biocatalyst are added to start the bioconversion. After completing of the bioconversion, the resulting acrylamide is present as well in said aqueous liquid.

The term "bioconversion" when used in the context of the present invention refers to a reaction, wherein acrylonitrile is converted to acrylamide in the presence of water and a biocatalyst. The term "biocatalytically prepared" when used herein refers to any method used to produce an aqueous acrylamide solution, wherein a bioconversion takes place.

As used with regard to any one of the embodiments described herein, the term "biocatalyst" comprises in particular microorganisms (e.g., bacteria or protozoic eukaryotes) and enzymes which are capable of converting acrylonitrile to acrylamide. Methods for determining the ability of a given biocatalyst (e.g., microorganism or enzyme) to convert acrylonitrile to acrylamide are well known in the art. The term "biocatalyst" may further comprise cellular material in the form of whole cells or fractured cells or part thereof including semi-purified and purified enzyme preparations and optional comprises fermentation broth. The cellular material may include any of the constituents of a microbial cell, for instance including cell wall material, cell nucleic acid material (for instance DNA or RNA), cytoplasma or proteins.

In accordance with any one of the methods of the present invention, the biocatalyst capable of converting acrylonitrile to acrylamide may be a microorganism which encodes the enzyme nitrile hydratase and having nitrile hydratase activity. With this regard, it is not relevant for the present invention whether the microorganism is naturally encoding nitrile hydratase, or whether it has been genetically modified to encode said enzyme, or whether a microorganism naturally encoding nitrile hydratase has been modified such as to be able to produce more and/or enhanced nitrile hydratase. As used herein, the expression "biocatalyst (e.g., microorganism) encoding (the enzyme) nitrile hydratase" or the like generally means that such a microorganism is generally also able to produce and stably maintain nitrile hydratase. That is, as used herein and as readily understood by the skilled person, a biocatalyst (e.g., a microorganism) to be employed in accordance with the present invention which (naturally or non-naturally) encodes nitrile hydratase is generally also capable of producing and stably maintaining nitrile hydratase. However, in accordance with the present invention, it is also possible that such microorganisms only produced nitrile hydratase during cultivation (or fermentation) of the microorganism—thus then containing nitrile hydratase—before being added to a reactor according to step (a) of any one of the methods described and provided herein. In such a case, it is possible that the microorganisms do not produce nitrile hydratase during the methods described and provided herein any more, but they act only via the nitrile hydratase units which they have produced before and which they still contain. As readily understood by the person skilled in the art, it is also possible that some nitrile hydratase molecules may leave the microorganism (e.g., due to lysis of the microorganism) and act freely in the solution as biocatalyst. As such, it also possible that the term "biocatalyst" as used herein encompasses the enzyme nitrile hydratase per se, as long as it is able to convert acrylonitrile to acrylamide as described and exemplified herein. In context with the present invention, it is also possible to directly employ nitrile hydratase as biocatalyst.

In context with the present invention, microorganism naturally encoding nitrile hydratase, which can be used as biocatalyst in any one of the methods described herein, comprise species belonging to a genus selected from the group consisting of *Rhodococcus, Aspergillus, Acidovorax, Agrobacterium, Bacillus, Bradyrhizobium, Burkholderia, Klebsiella, Mesorhizobium, Moraxella, Pantoea, Pseudomonas, Rhizobium, Rhodopseudomonas, Serratia, Amycolatopsis, Arthrobacter, Brevibacterium, Corynebacterium, Microbacterium, Micrococcus, Nocardia, Pseudonocardia, Trichoderma, Myrothecium, Aureobasidium, Candida, Cryptococcus, Debaryomyces, Geotrichum, Hanseniaspora, Kluyveromyces, Pichia, Rhodotorula, Escherichia, Geobacillus, Comomonas*, and *Pyrococcus*. In preferred embodiments of the invention the biocatalyst is selected from bacteria of the genus *Rhodococcus, Pseudomonas, Escherichia* and *Geobacillus*.

Preferred biocatalysts to be employed in context with any one of the methods of the present invention comprise representatives of the genus *Rhodococcus*. Species suitable as biocatalyst to be employed in context with any one of the methods of the present invention may comprise, e.g., *Rhodococcus rhodochrous* (e.g., NCIMB 41164 or J1/FERM-BP 1478, M8 (Accession number: VKPMB-5926), M33), *Rhodococcus pyridinovorans, Rhodococcus erythropolis, Rhodococcus equi, Rhodococcus ruber, Rhodococcus opacus, Aspergillus niger, Acidovorax avenae, Acidovorax facilis, Agrobacterium tumefaciens, Agrobacterium radiobacter, Bacillus subtilis, Bacillus pallidus, Bacillus smithii, Bacillus* sp BR449, *Bradyrhizobium oligotrophicum, Bradyrhizobium diazoefficiens, Bradyrhizobium japonicum, Burkholderia cenocepacia, Burkholderia gladioli, Klebsiella oxytoca, Klebsiella pneumonia, Klebsiella variicola, Mesorhizobium ciceri, Mesorhizobium opportunistum, Mesorhizobium* sp F28, *Moraxella, Pantoea endophytica, Pantoea agglomerans, Pseudomonas chlororaphis, Pseudomonas putida, Rhizobium, Rhodopseudomonas palustris, Serratia liquefaciens, Serratia marcescens, Amycolatopsis, Arthrobacter, Brevibacterium* sp CH1, *Brevibacterium* sp CH2, *Brevibacterium* sp R312, *Brevibacterium imperiale, Brevibacterium casei, Corynebacterium nitrilophilus, Corynebacterium pseudodiphteriticum, Corynebacterium glutamicum, Corynebacterium hoffmanii, Microbacterium imperiale, Microbacterium smegmatis, Micrococcus luteus, Nocardia globerula, Nocardia rhodochrous, Nocardia* sp 163, *Pseudonocardia thermophila, Trichoderma, Myrothecium verrucaria, Aureobasidium pullulans, Candida famata, Candida guilliermondii, Candida tropicalis, Cryptococcus flavus, Cryptococcus* sp UFMG-Y28, *Debaryomyces hanseii, Geotrichum candidum, Geotrichum* sp JR1, *Hanseniaspora, Kluyveromyces thermotolerans, Pichia kluyveri, Rhodotorula glutinis, Comomonas testosteroni, Pyrococcus abyssi, Pyrococcus furiosus, Escherichia coli* MT-10822 (Accession number: FERM BP-5785), *Geobacillus* sp. RAPc8, or *Pyrococcus horikoshii*. The above microorganisms can be cultured by any method that is appropriate for a given microbial species. According to a preferred embodiment of the methods of the present invention, the biocatalyst to be employed belongs to the species *Rhodococcus rhodochrous*. Particular examples for strains belonging to *Rhodococcus rhodochrous* which may be employed in context with any one of the methods of the present invention comprise NCIMB 41164, J1 (FERM-BP 1478), M8 (Accession number: VKPMB-5926), and M33. Alternatively or in addition to *Rhodococcus rhodocrous*, the biocatalyst employed in any one of the methods described herein may be *Rhodococcus pyridinovorans*. Alternatively or in addition, the biocatalyst may be *Escherichia coli* MT-10822 (Accession number: FERM BP-5785).

According to the present invention, combinations of these microorganisms can be used as well. Further, the above microorganisms can be cultured by any method that is appropriate for a given microbial species. The microbial biocatalyst of the present invention that is prepared from microorganisms refers to a culture solution obtained by culturing microorganisms, cells obtained by a harvesting process or the like, cell disrupted by ultrasonication or the like, or those prepared after cell disruption including a crude enzyme, a partially-purified enzyme or a purified enzyme. A mode to use the microbial catalyst may be appropriately selected depending on enzyme stability, production scale and the like.

In some embodiments of the present invention, the biocatalyst used for converting acrylonitrile to acrylamide as described herein may be washed before the use in said reaction. In some embodiments, the biocatalyst may be washed once with water, a buffer or the like, and then washed with acrylic acid before the reaction. In some embodiments the biocatalyst used herein is washed with acrylic acid before the reaction as described in detail in EP1380652. In some embodiments the biocatalyst may be washed with acrylic acid immediately before the reaction. Further, any washing methods can be employed. Examples of such a method that can be applied according to the present invention include a method which involves repeated washing and centrifugation, and a washing method using a hollow fiber membrane. Further, immobilized biocatalysts can be washed by repeating agitation and precipitation of the immobilized catalysts in a wash and the removal of supernatant. Any washing method and any number of washing can be appropriately set in consideration of washing efficiency, enzyme stability and the like. The concentration of acrylic acid to be used for washing is preferably between 0.01% by mass and 10% by mass in an aqueous acrylic solution. More preferably, the concentration is between 0.05% by mass and 1% by mass, and most preferably is 0.1% by mass.

In context with the present invention, nitrile hydratase encoding microorganisms which are not naturally encoding nitrile hydratase may be genetically engineered microorganisms which naturally do not contain a gene encoding a nitrile hydratase but which have been manipulated such as to contain a polynucleotide encoding a nitrile hydratase (e.g., via transformation, transduction, transfection, conjugation, or other methods suitable to transfer or insert a polynucleotide into a cell as known in the art; cf. Sambrook and Russell 2001, Molecular Cloning: A Laboratory Manual, CSH Press, Cold Spring Harbor, N.Y., USA), thus enabling the microorganisms to produce and stably maintain the nitrile hydratase enzyme. For this purpose, it may further be required to insert additional polynucleotides which may be necessary to allow transcription and translation of the nitrile hydratase gene or mRNA, respectively. Such additional polynucleotides may comprise, inter alia, promoter sequences, polyT- or polyU-tails, or replication origins or other plasmid-control sequences. In this context, such genetically engineered microorganisms which naturally do not contain a gene encoding a nitrile hydratase but which have been manipulated such as to contain a polynucleotides encoding a nitrile hydratase may be prokaryotic or eukaryotic microorganisms. Examples for such prokaryotic microorganisms include, e.g., representatives of the species *Escherichia coli*. Examples for such eukaryotic microorganisms include, e.g., yeast (e.g., *Saccharomyces cerevisiae*).

In context of the present invention, the term "nitrile hydratase" (also referred to herein as NHase) generally means an enzyme which is capable of catalyzing the conversion (i.e. hydration) of acrylonitrile to acrylamide. Such an enzyme may be, e.g., the enzyme registered under IUBMB nomenclature as of Apr. 1, 2014: EC 4.2.1.84; CAS-No. 2391-37-5. However, the term "nitrile hydratase" as used herein also encompasses modified or enhanced enzymes which are, e.g., capable of converting acrylonitrile to acrylamide more quickly, or which can be produced at a higher yield/time-ratio, or which are more stable, as long as they are capable to catalyze conversion (i.e. hydration) of acrylonitrile to acrylamide. Methods for determining the ability of a given biocatalyst (e.g., microorganism or enzyme) for catalyzing the conversion of acrylonitrile to acrylamide are known in the art. As an example, in context with the present invention, activity of a given biocatalyst to act as a nitrile hydratase in the sense of the present invention may be determined as follows: First reacting 100 µl of a cell suspension, cell lysate, dissolved enzyme powder or any other preparation containing the supposed nitrile hydratase with 875 µl of an 50 mM potassium phosphate buffer and 25

μl of acrylonitrile at 25° C. on an eppendorf tube shaker at 1,000 rpm for 10 minutes. After 10 minutes of reaction time, samples may be drawn and immediately quenched by adding the same volume of 1.4% hydrochloric acid. After mixing of the sample, cells may be removed by centrifugation for 1 minute at 10,000 rpm and the amount of acrylamide formed is determined by analyzing the clear supernatant by HPLC. For affirmation of an enzyme to be a nitrile hydratase in context with the present invention, the concentration of acrylamide shall be between 0.25 and 1.25 mmol/l—if necessary, the sample has to be diluted accordingly and the conversion has to be repeated. The enzyme activity may then be deduced from the concentration of acrylamide by dividing the acrylamide concentration derived from HPLC analysis by the reaction time, which has been 10 minutes and by multiplying this value with the dilution factor between HPLC sample and original sample. Activities >5 U/mg dry cell weight, preferably >25 U/mg dry cell weight, more preferably >50 U/mg dry cell weight, most preferably >100 U/mg dry cell weight indicate the presence of a functional biocatalyst and are considered as biocatalyst capable of converting acrylonitrile to acrylamide in context with the present invention.

In context with the present invention, the nitrile hydratase may be a polypeptide encoded by a polynucleotide which comprises or consists of a nucleotide sequence which is at least 70%, preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identical to the nucleotide sequence of SEQ ID NO: 1 (alpha-subunit of nitrile hydratase of *Rhodococcus rhodochrous*: GTGAGCGAGCACGTCAATAAGTACACGGAGTACGAGGCACGTACCAAGGCGATCGAAACCTTGCTGTACGAGCGAGGGCTCATCACGCCCGCCGCGGTCGACCGAGTCGTTTCGTACTACGAGAACGAGATCGGCCCGATGGGCGGTGCCAAGGTCGTGGCCAAGTCCTGGGT GGACCCTGAGTACCGCAAGTGGCTCGAAGAGGACGCGACGGCCGCGATGGCGTCATT GGGCTATGCCGGTGAGCAGGCACACCAAATTTCGGCGGTCTTCAACGACTCCCAAACG CATCACGTGGTGGTGTGCACTCTGTGTTCGTGCTATCC GTGGCCGGTGCTTGGTCTCC CGCCCGCCTGGTACAAGAGCATGGAGTACCGGTCCCGAGTGGTAGCGGACCCTCGTG GAGTGCTCAAGCGCGATTTCGGTTTCGACATCCCCGATGAGGTGGAGGTCAGGGTTTG GGACAGCAGCTCCGAAATCCGCTACATCGTCATCCCGGAACGGCCGGCCGGCACCGA CGGTTGGTCCGAGGAGGAGCTGACGAAGCTGGTGAGCCGGGACTCGATGATCGGTGT CAGTAATGCGCTCACACCGCAGGAAGTGATCGTATGA) and/or to the nucleotide sequence of SEQ ID NO: 3 (beta-subunit of nitrile hydratase of *Rhodococcus rhodochrous*: ATGGATGGTATCCACGACACAGGCGGCATGACCGGATACGGACCGGTCCCCTATCAGA AGGACGAGCCCTTCTTCCACTACGAGTGGGAGGGTCGGACCCTGTCAATTCTGACTTG GATGCATATCTGGTGGGACAAGTCGCGGTTCTTCCGGG AGTCGATG GGGAACGAAAACTACGTCAACGAGATTCGCAACTCGTACTACACCCACTGGCTGAGTG CGGCAGAACGTATCCTCGTCGCCGACAAGATCATCACCGAAGAAGAGCGAAAGCACCG TGTGCAAGAGATCCTTGAGGGTCGGTACACGGACAGGAAGCCGTCGCGGAAGTTCGAT CCGGCCCAGATCGAGAAGGCGATCGAACGGCTTCACGAGCCCCACTCCCTAGCGCTTC CAGGAGCGGAGCCGAGTTTCTCTCTCGGTGACAAGATCAAAGTGAAGAGTATGAACCC GCTGGGACACACACGGTGCCCGAAATATGTCGGAACAAGATCGGGGAAATCGTCGCC TACCACGGCTGCCAGATCTATCCCGAGAGCAGCTCCGCCGGCCTCGGCGACGA TCCTC GCCCGCTCTACACGGTCGCGTTTTCCGCCCAGGAACTGTGGGGCGACGACGGAAACG GGAAAGACGTAGTGTGCGTCGATCTCTGGGAACCGTACCT GATCTCTGCGTGA), provided that the polypeptide encoded by said polynucleotide is capable of catalyzing hydration of acrylonitrile to acrylamide (i.e. has nitrile hydratase activity) as described and exemplified herein. Also in the context with the present invention, the nitrile hydratase may be a polypeptide which comprises or consists of an amino acid sequence which is at least 70%, preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identical to the amino acid sequence of SEQ ID NO: 2 (alpha-subunit of nitrile hydratase of *Rhodococcus rhodochrous*: VSEHVNKYTE YEARTKAIET LLYERGLITP AAVDRVVSYY ENEIGPMGGA KVVAKSWVDP EYRKWLEEDA TAAMASLGYA GEQAHQISAV FNDSQTHHVV VCTLCSCYPW PVLGLPPAWY KSMEYRSRVV ADPRGVLKRD FGFDIPDEVE VRVWDSSSEI RYIVIPERPA GTDGWSEEEL TKLVSRDSMI GVSNALTPQE VIV) and/or to the amino acid sequence of SEQ ID NO: 4 (beta-subunit of nitrile hydratase of *R. rhodochrous*: MDGIHDTGGM TGYGPVPYQK DEPFFHYEWE GRTLSILTWM HLKGISWWDK SRFFRESMGN ENYVNEIRNSY YTHWLSAAE RILVADKIIT EEERKHRVQE ILEGRYTDRK PSRKFDPAQI EKAIERLHEP HSLALPGAEP SFSLGDKIKV KSMNPLGHTR CPKYVRNKIG EIVAYHGCQI YPESSSAGLG DDPRPLYTVA FSAQELWGDD GNGKDVVCVD LWEPYLISA), provided that said polypeptide is capable of catalyzing hydration of acrylonitrile to acrylamide as described and exemplified herein.

The level of identity between two or more sequences (e.g., nucleic acid sequences or amino acid sequences) can be easily determined by methods known in the art, e.g., by BLAST analysis. Generally, in context with the present invention, if two sequences (e.g., polynucleotide sequences or amino acid sequences) to be compared by, e.g., sequence comparisons differ in identity, then the term "identity" may refer to the shorter sequence and that part of the longer sequence that matches said shorter sequence. Therefore, when the sequences which are compared do not have the same length, the degree of identity may preferably either refer to the percentage of nucleotide residues in the shorter sequence which are identical to nucleotide residues in the longer sequence or to the percentage of nucleotides in the longer sequence which are identical to nucleotide sequence in the shorter sequence. In this context, the skilled person is readily in the position to determine that part of a longer sequence that matches the shorter sequence. Furthermore, as used herein, identity levels of nucleic acid sequences or amino acid sequences may refer to the entire length of the respective sequence and is preferably assessed pair-wise, wherein each gap is to be counted as one mismatch. These definitions for sequence comparisons (e.g., establishment of "identity" values) are to be applied for all sequences described and disclosed herein.

Moreover, the term "identity" as used herein means that there is a functional and/or structural equivalence between the corresponding sequences. Nucleic acid/amino acid sequences having the given identity levels to the herein-described particular nucleic acid/amino acid sequences may represent derivatives/variants of these sequences which, preferably, have the same biological function. They may be either naturally occurring variations, for instance sequences from other varieties, species, etc., or mutations, and said mutations may have formed naturally or may have been produced by deliberate mutagenesis. Furthermore, the variations may be synthetically produced sequences. The variants may be naturally occurring variants or synthetically produced variants or variants produced by recombinant DNA techniques. Deviations from the above-described nucleic acid sequences may have been produced, e.g., by deletion, substitution, addition, insertion and/or recombination. The term "addition" refers to adding at least one nucleic acid residue/amino acid to the end of the given sequence, whereas "insertion" refers to inserting at least one nucleic acid residue/amino acid within a given sequence. The term "deletion" refers to deleting or removal of at least one nucleic acid residue or amino acid residue in a given sequence. The term "substitution" refers to the replacement of at least one nucleic acid residue/amino acid residue in a given sequence. Again, these definitions as used here apply, mutatis mutandis, for all sequences provided and described herein.

Generally, as used herein, the terms "polynucleotide" and "nucleic acid" or "nucleic acid molecule" are to be construed synonymously. Generally, nucleic acid molecules may comprise inter alia DNA molecules, RNA molecules, oligonucleotide thiophosphates, substituted ribo-oligonucleotides or PNA molecules. Furthermore, the term "nucleic acid molecule" may refer to DNA or RNA or hybrids thereof or any modification thereof that is known in the art (see, e.g., U.S. Pat. Nos. 5,525,711, 4,711,955, 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mitochondrial DNA, mRNA, antisense RNA, ribozymal RNA or a DNA encoding such RNAs or chimeroplasts (Gamper, Nucleic Acids Research, 2000, 28, 4332-4339). Said polynucleotide sequence may be in the form of a vector, plasmid or of viral DNA or RNA. Also described herein are nucleic acid molecules which are complementary to the nucleic acid molecules described above and nucleic acid molecules which are able to hybridize to nucleic acid molecules described herein. A nucleic acid molecule described herein may also be a fragment of the nucleic acid molecules in context of the present invention. Particularly, such a fragment is a functional fragment. Examples for such functional fragments are nucleic acid molecules which can serve as primers.

When adding the biocatalyst to the reactor in any one of the methods of the present invention, the biocatalyst may be taken directly from the fermentation broth. Alternatively the biocatalyst may be dried before. With this respect, the biocatalyst may be dried before being added to the reactor according to any one of the methods of the present invention. In this context the term "before" does not necessarily mean that the biocatalyst has been dried and is then immediately added to the reactor. It is rather sufficient that the biocatalyst has undergone a drying step at any time before it is added to the reactor, independently of whether further steps between the drying and the addition are performed or not. As non-limiting examples, such further steps between the drying step and the addition to the reactor may be storage or reconstitution. However, it is also possible to add the biocatalyst to the reactor directly after drying. The inventors have found that by using a biocatalyst, which has undergone a drying step, the concentration of acrylic acid in an aqueous acrylamide solution obtained by any one of the methods described herein is further reduced in comparison to the case that a biocatalyst is used which has not undergone drying before being employed in the bioconversion.

Regarding the drying method, in any one of the methods for preparing an aqueous acrylamide solution or for reducing the acrylic acid concentration of an aqueous acrylamide solution a biocatalyst may be used which has been dried using freeze-drying, spray drying, heat drying, vacuum drying, fluidized bed drying and/or spray granulation, wherein spray drying is preferred. With this respect, spray drying is preferred, since by using a biocatalyst, which has been subjected to spray drying, in general a higher reduction of the acrylic acid concentration in the obtained aqueous acrylamide solutions is achieved compared to using a biocatalyst which has been dried using other methods.

According to any one of the methods of the present invention a dry biocatalyst may be used. This means that the biocatalyst may be added to the reactor in a dry form. For example, the catalyst may be added in a dry form in step (a) of any of the methods disclosed herein. In particular, the biocatalyst may have the form of a powder or a granule. Alternatively, the dried biocatalyst may be reconstituted before being added in step (a) of any of the methods described herein. For example, the biocatalyst may be reconstituted by suspending in an aqueous composition. With this respect, the biocatalyst may be suspended in water or a buffer. As a further alternative, a biocatalyst in form of a matrix bound microorganism may be added in step (a) of any of the methods disclosed herein. The term "dried biocatalyst" or "dry biocatalyst" as used herein refers to a biocatalyst that has been subjected to a drying step. A dried biocatalyst typically has a moisture content of less than about 20 w/w %, more preferably less than about 15 w/w %, even more preferably less than about 14 w/w %, most preferably from about 5 to about 10 w/w % based on the total weight of the biocatalyst sample. Methods of determining the moisture content are familiar to the skilled person. For example, in the context of the present invention the moisture content of a sample of the dried biocatalyst may be determined via thermogravimetric analysis. At the beginning of the thermogravimetric analysis the initial weight of the sample is determined. The sample is then heated and the moisture vaporizes. Heating is continued until the sample weight remains constant. The difference between the constant weight at the end of the analysis and the initial weight represents the amount of water vaporized during the analysis, which allows for calculation of the moisture content of the sample. For determination of the moisture content via thermogravimetric analysis, the biocatalyst sample may be, for example, analyzed on a 'Mettler Toledo HB43-S Halogen moisture analyzer', operated at 130° C. until the sample weight remains constant for at least 30 seconds.

Since the present invention allows for the preparation of a polyacrylamide solution having increased viscosity and thus exhibiting improved physical properties, the present invention also encompasses a method for increasing the viscosity of a polyacrylamide solution when compared to a reference solution, the method comprising using an aqueous acrylamide solution having an $OD_{600}$ of equal to or less than 0.6, preferably of equal to or less than 0.5, more preferably of equal to or less than 0.4, even more preferably of equal to or less than 0.3, still more preferably of equal to or less than 0.2, still more preferably of equal to or less than 0.1, most preferably of equal to or less than 0.05. The aqueous acrylamide solution used in the described method is essentially produced by converting acrylonitrile to acrylamide using a biocatalyst, and separating said biocatalyst from the aqueous acrylamide solution after completion of the conversion of acrylonitrile to acrylamide as described elsewhere herein.

Generally, the present invention relates to all the embodiments described herein as well as to all permutations and combinations thereof. Any particular aspect or embodiments described herein must not be construed as limiting the scope of the present invention on such aspects or embodiments.

Moreover, the invention refers to a method for producing an acrylamide solution comprising the following steps:
(a) preparing an aqueous acrylamide solution by converting acrylonitrile to acrylamide using a biocatalyst,
(b) separating the biocatalyst from the aqueous acrylamide solution of step (a) such that the $OD_{600}$ of the aqueous acrylamide solution is equal to or less than 0.6.

In addition, the invention refers to a method for producing an acrylamide solution comprising the following steps:
(a) preparing an aqueous acrylamide solution by converting acrylonitrile to acrylamide using a biocatalyst,
(b) separating the biocatalyst from the aqueous acrylamide solution of step (a) by disc stack separation performed with a feed flow rate of less than 600 l/h, preferably less than 500 l/h, more preferably less than 400 l/h, even more preferably less than 300 l/h, still more preferably less than 200 l/h or 100 l/h.

In particular, the invention refers to a method for producing an acrylamide solution comprising the following steps:
(a) preparing an aqueous acrylamide solution by converting acrylonitrile to acrylamide using a biocatalyst,
(b) separating the biocatalyst from the aqueous acrylamide solution of step (a) by disc stack separation performed with specific settling area of more than 19.67 $m^2h/l$, preferably a specific settling area of more than 23.6 $m^2h/l$, more preferably with a specific settling area of more than 29.5 $m^2h/l$, even more preferably with a specific settling area of more than 39.3 $m^2h/l$, still more preferably with a specific settling area of more than 59.0 $m^2h/l$, most preferably with a specific settling area of more than 118.0 $m^2h/l$.

Another aspect refers to a method for preparing a polyacrylamide solution prepared by biocatalyzed conversion of acrylonitrile to acrylamide comprising the following steps:
(a) preparing an aqueous acrylamide solution by converting acrylonitrile to acrylamide using a biocatalyst,
(b) separating the biocatalyst from the aqueous acrylamide solution of step (a) by disc stack separation performed with specific settling area of more than 19.67 m2h/l, preferably a specific settling area of more than 23.6 m2h/l, more preferably with a specific settling area of more than 29.5 m2h/l, even more preferably with a specific settling area of more than 39.3 m2h/l, still more preferably with a specific settling area of more than 59.0 m2h/l, most preferably with a specific settling area of more than 118.0 m2h/l.
(c) polymerizing the aqueous acrylamide solution obtained in step (b) to polyacrylamide.

Further, the invention refers to the use of an aqueous acrylamide solution having an $OD_{600}$ equal to or less than 0.6, for increasing the viscosity of a polyacrylamide solution prepared from said acrylamide solution.

Further, the invention refers to the use of an aqueous acrylamide solution having an $OD_{600}$ equal to or less than 0.6, for increasing the viscosity of a polyacrylamide solution prepared from said acrylamide solution, wherein the $OD_{600}$ is measured directly after separating a biocatalyst from the aqueous acrylamide solution.

The $OD_{600}$ is measured directly after separating that biocatalyst from the aqueous acrylamide solution means, that the $OD_{600}$ value is achieved by the separation of the biocatalyst and not by other measures such as dilution of the aqueous acrylamide solution.

EXAMPLES

The following examples illustrate the invention. These examples should not be construed as to limit the scope of this invention. The examples are included for purposes of illustration and the present invention is limited only by the claims. It will be clear to a skilled person in the art that the invention may be practiced in other ways than as particularly described in the present description and examples. Numerous modifications and variations of the present invention are possible in light of the above teachings and, therefore, are within the scope of the appended claims.

Hydration

The biocatalyst *Rhodococcus rhodochrous* (strain NCIMB 41164) has been used for the hydration of acrylonitrile to acrylamide. The exothermic reaction was carried out in a stirred tank reactor with acrylonitrile inflow and cooling circuit. The reaction was initiated by addition of biocatalyst and acrylonitrile. The addition of acrylonitrile can be adequately monitored by FTIR analysis. The starting material was added until the desired acrylamide concentration was achieved.

Separation

For the separation step a disc stack separator (BTPX 205, Alfa Laval) was utilized. The equivalent clarification surface amounted to 11800 $m^2$. The separator was used with a rotation speed of about 9650 UPM and the infeed volumetric feed flow rate of the suspension was in the range of about 100-1000 l/h. In the range of 100 l/h-500 l/h MPFR-values according to API RP 63 of less than 1.3 at a filter pore diameter of 1.2 µm, 2 µm, 3 µm and 5 µm could be achieved (see Tables 1 and 2).

$OD_{600}$ Measurements

The optical density of the aqueous acrylamide solution at 600 nm ($OD_{600}$) was measured after separation of the biocatalyst from the reaction mixture in order to determine the remaining amount of biomass. Tables 1 and 2 show the dependence of $OD_{600}$ values of the aqueous acrylamide solution on the feed flow rate when using a disc stack separator and applying feed flow rates of 100-600 l/h, corresponding to specific settling areas of 118.0-19.67 $m^2$h/l. Demin. water was used as reference sample in these measurements. $OD_{600}$ measurements were performed using a Shimadzu Europe UV-1650PC double-beam spectrophotometer, wherein the standard cuvette slide was exchanged by a six-fold cuvettes slide (CPS-Controller CPS-240A). The samples were measured in standard 1 cm light path semi-micro PS cuvettes.

Determination of the Filterability—MPFR (Millipore Filtration Ratio)

The filterability of the acrylamide copolymers was investigated by using MPFR-values. The MPFR-value (Millipore filtration ratio) indicates the deviation of a polymer solution from ideal filtration behavior, where the ideal filtration behavior has no decrease in the filtration rate when adding the filter. For determining the MPFR-values about 200 ml of polymer solution with a concentration of 1,000 ppm at a pressure of $1.38*10^5$ Pa were filtered through a polycarbonate filter with a pore size of 5 microns. The amount of the filtrate was time-dependent recorded. The calculation of the MPFR-value was effected according to the following formula:

$$MPFR = (t_{180\,g} - t_{160\,g})/(T_{80\,g} - t_{60\,g}),$$

wherein $t_{index}$ is the time at which the specified amount of filtrate was measured, i.e. $t_{180\,g}$ is the time at which 180 g filtrate was measured. According to API RP 63 ("Recommended Practices for Evaluation of Polymers Used in Enhanced Oil Recovery Operations", American Petroleum Institute), values less than 1.3 are acceptable. In case of an ideal filterability the MPFR-value is 1.

Polymerization

In a plastic bucket with a magnetic stirrer, a pH-meter and a thermometer, 112.8 g of 35% sodium acrylate solution were present, and subsequently consecutively added 108.33 g of distilled water, 154.84 g of the acrylamide solution (52%) achieved after separation, 1.2 g Trilon C solution (5%) and 4 ml of an ACVA (4,4'-azobis(4-cyanovaleric acid)) solution (4%). After adjusting the pH of the solution to 6.75, using 20% or 2% sulfuric acid solution and adding the residual amount of water (total amount of 131.6 g minus the amount of water already added, minus the amount of acid needed), the monomer solution was adjusted to a temperature of 4° C. The solution was transferred into a thermo flask, the temperature sensor was mounted, and rinsed with nitrogen for 30 min. Using 1 ml of an AIBN (azobisisobutyronitrile) solution in methanol (4%), 0.1 ml of a t-BHP (tert-butyl hydroperoxide) solution (1%) and 0.2 ml of a sodium sulfite solution (1%), the polymerization was started. Subsequently, the gel block was crushed using a meat grinder, and the obtained gel granules were dried for 2 hours at 55° C. using a fluid-bed dryer. It was obtained a white and hard granule material, which was transferred in a powdery state using a centrifugal mill.

The filterability of a 2000 ppm polymer solution prepared by the preparation example described herein was measured in artificial sea water. MPFR-values were determined as described herein above. The measurement of the viscosity of a 4000 ppm polymer solution was carried out as well in artificial sea water. The ppm values refer to weight parts based on the total weight of the polymer solution. The viscosity is measured at a shear rate of 7 l/s at 25° C.+/−1° C. at a rheometer (Anton Paar MCR 301/2) with DIN double gap geometry. Filterability and viscosity values are depicted in Tables 1 and 2. The ppm values are based on the total weight of the polymer solution.

TABLE 1

| Feed flow rate to separator [l/h] | Specific settling area* [m²/(l/h)] | Batch #P3 | | | | | |
|---|---|---|---|---|---|---|---|
| | | OD$_{600}$ | MPFR 5 μm | MPFR 3 μm | MPFR 2 μm | MPFR 1.2 μm | Viscosity [mPas] |
| 100 | 118 | 0.042 | 1.0 | 1.0 | 1.0 | 1.0 | 69 |
| 200 | 59 | 0.052 | 1.0 | 1.0 | 1.0 | 1.0 | 68 |
| 300 | 39.3 | 0.057 | 1.0 | 1.0 | 1.0 | 1.0 | 63 |
| 400 | 29.5 | 0.071 | 1.03 | 1.1 | 1.27 | 1.38 | 62 |
| 500 | 23.6 | 0.108 | 1.13 | 1.21 | 1.38 | 1.56 | 60 |
| 600 | 19.67 | 0.26 | | Not measured | | | |
| 800 | 14.75 | 0.45 | | Not measured | | | |
| 1000 | 11.8 | 0.64 | 1.26 | 1.38 | 1.59 | 2.03 | 51 |

TABLE 2

| Feed flow rate to separator [l/h] | Specific settling area* [m²/(l/h)] | Batch #P4 | | | | | |
|---|---|---|---|---|---|---|---|
| | | OD$_{600}$ | MPFR 5 μm | MPFR 3 μm | MPFR 2 μm | MPFR 1.2 μm | Viscosity [mPas] |
| 100 | 118 | 0.032 | 1.0 | 1.0 | 1.0 | 1.0 | 69 |
| 200 | 59 | 0.032 | 1.0 | 1.0 | 1.0 | 1.0 | 68 |
| 300 | 39.3 | 0.035 | 1.0 | 1.0 | 1.0 | 1.0 | 66 |
| 400 | 29.5 | 0.038 | 1.0 | 1.0 | 1.05 | 1.1 | 65 |
| 500 | 23.6 | 0.047 | 1.0 | 1.0 | 1.06 | 1.13 | 62 |
| 600 | 19.67 | 0.09 | 1.1 | 1.15 | 1.35 | 1.53 | 60 |
| 800 | 14.75 | 0.33 | 1.21 | 1.32 | 1.51 | 1.89 | 56 |
| 1000 | 11.8 | — | — | — | — | — | — |

*"Specific settling area" is defined as the equivalent settling area of the disc stack centrifuge divided by the feed flow rate.

Table 1 and Table 2 show OD600, MPFR MPFR-values according to API 63 (filterability) of a 2000 ppm polyacrylamide solution and Viscosity values of a 4000 ppm polyacrylamide solution of aqueous acrylamide solutions in dependence on the feed flow rate and the specific settling area when using a disc stack separator to separate the biocatalyst from the aqueous acrylamide solution for different batches. The aqueous acrylamide solution was biocatalytically prepared by hydrating acrylonitrile to acrylamide and the used biocatalyst was separated prior to polymerization using different feed flow rates. Batch #3 and Batch #4 represent different reaction-discharges at different time points of the separation. The polyacrylamide was dissolved in artificial sea water, respectively, and the data shown are mean values from 3 to 4 individual measurements.

What is claimed is:

1. A method for producing a polyacrylamide solution having an increased viscosity relative to a reference solution, the method comprising:
   (a) preparing an aqueous acrylamide solution by converting acrylonitrile to acrylamide using a biocatalyst,
   (b) separating the biocatalyst from the aqueous acrylamide solution of (a) to obtain an aqueous acrylamide solution having an optical density at 600 nm equal to or less than 0.6, and
   (c) polymerizing the aqueous acrylamide solution obtained in (b) to obtain a polyacrylamide,
   wherein the reference solution is a polyacrylamide solution prepared from an aqueous acrylamide solution having an optical density at 600 nm of more than 0.6 and wherein the reference solution is prepared by the same method without separating the biocatalyst, and wherein the separation of the biocatalyst is performed by centrifugation.

2. The method according to claim 1, further comprising at least one of:
   (d) drying the polyacrylamide;
   (e) shredding and/or squelching the polyacrylamide; and/or
   (f) dissolving the polyacrylamide in an aqueous solution.

3. The method according to claim 1, wherein the biocatalyst of (a) is not immobilized.

4. The method according to claim 1, wherein the optical density is measured directly after separating the biocatalyst.

5. The method according to claim 1, wherein the viscosity of the polyacrylamide solution is more than 60 mPas at room temperature when the polyacrylamide is dissolved in artificial seawater.

6. The method according to claim 5, wherein the viscosity of the polyacrylamide solution is less than 200 mPas when the polyacrylamide is dissolved in artificial seawater.

7. The method according to claim 1, wherein the separation of the biocatalyst is started within 30 minutes after completion of the conversion of acrylonitrile to acrylamide.

8. The method according to claim 1, wherein the biocatalyst is flocculated prior to separation.

9. The method according to claim 1, wherein the centrifugation is performed by disc stack separation.

10. The method according to claim 1, wherein the separation is performed such that a specific settling area is 19.67 $m^2h/l$ or more.

11. The method according to claim 1, wherein the aqueous acrylamide solution obtained in (b) has an optical density at 600 nm of 0.001 or more.

12. The method according to claim 1, wherein the biocatalyst is a biocatalyst having nitrile hydratase activity.

13. The method according to claim 12, wherein the biocatalyst having nitrile hydratase activity comprises microorganisms of a genus selected from the group consisting of *Rhodococcus, Aspergillus, Acidovorax, Agrobacterium, Bacillus, Bradyrhizobium, Burkholderia, Klebsiella, Mesorhizobium, Moraxella, Pantoea, Pseudomonas, Rhizobium, Rhodopseudomonas, Serratia, Amycolatopsis, Arthrobacter, Brevibacterium, Corynebacterium, Microbacterium, Micrococcus, Nocardia, Pseudonocardia, Trichoderma, Myrothecium, Aureobasidium, Candida, Cryptococcus, Debaryomyces, Geotrichum, Hanseniaspora, Kluyveromyces, Pichia, Rhodotorula, Escherichia, Geobacillus, Comomonas,* and *Pyrococcus*, and/or wherein the biocatalyst having nitrile hydratase activity comprises transformed microbial cells comprising a nitrile hydratase gene.

14. The method according to claim 13, wherein the biocatalyst having nitrile hydratase activity comprises microorganisms of a genus selected from the group consisting of *Rhodococcus, Pseudomonas, Escherichia* and *Geobacillus*.

15. The method according to claim 14, wherein the biocatalyst having nitrile hydratase activity comprises microorganisms of a species selected from the group consisting of *Rhodococcus rhodochrous, Rhodococcus erythropolis, Rhodococcus equi, Rhodococcus ruber, Rhodococcus opacus, Rhodococcus pyridinovorans, Aspergillus niger, Acidovorax avenae, Acidovorax facilis, Agrobacterium tumefaciens, Agrobacterium radiobacter, Bacillus subtilis, Bacillus pallidus, Bacillus smithii, Bacillus sp BR449, Bradyrhizobium oligotrophicum, Bradyrhizobium diazoefficiens, Bradyrhizobium japonicum, Burkholderia cenocepacia, Burkholderia gladioli, Klebsiella oxytoca, Klebsiella pneumonia, Klebsiella variicola, Mesorhizobium ciceri, Mesorhizobium opportunistum, Mesorhizobium* sp F28, *Moraxella, Pantoea endophytica, Pantoea agglomerans, Pseudomonas chlororaphis, Pseudomonas putida, Rhizobium, Rhodopseudomonas palustris, Serratia liquefaciens, Serratia marcescens, Amycolatopsis, Arthrobacter, Brevibacterium* sp CHI, *Brevibacterium* sp CH2, *Brevibacterium* sp R312, *Brevibacterium imperiale, Corynebacterium nitrilophilus, Corynebacterium pseudodiphteriticum, Corynebacterium glutamicum, Corynebacterium hoffmanii, Microbacterium imperiale, Microbacterium smegmatis, Micrococcus luteus, Nocardia globerula, Nocardia rhodochrous, Pseudonocardia thermophila, Trichoderma, Myrothecium verrucaria, Aureobasidium pullulans, Candida famata, Candida guilliermondii, Candida tropicalis, Cryptococcus jlavus, Cryptococcus* sp UFMG-Y28, *Debaryomyces hanseii, Geotrichum candidum, Geotrichum* sp JRI, *Hanseniaspora, Kluyveromyces thermotolerans, Pichia kluyveri, Rhodotorula glutinis, Escherichia coli, Geobacillus* sp. RAPc8, *Comomonas testosteroni, Pyrococcus abyssi, Pyrococcus fariosus,* and *Pyrococcus horikoshii*.

16. The method according to claim 15, wherein the biocatalyst having nitrile hydratase activity comprises microorganisms of the species *Rhodococcus rhodochrous*.

17. The method according to claim 1, wherein the biocatalyst has been dried before preparing the aqueous acrylamide solution of (a).

* * * * *

```
                         SEQUENCE LISTING

<160> NUMBER OF SEQ ID NOS: 4

<210> SEQ ID NO 1
<211> LENGTH: 612
<212> TYPE: DNA
<213> ORGANISM: Rhodococcus rhodochrous

<400> SEQUENCE: 1
gtgagcgagc acgtcaataa gtacacggag tacgaggcac gtaccaaggc gatcgaaacc      60
ttgctgtacg agcgagggct catcacgccc gccgcggtcg accgagtcgt ttcgtactac     120
gagaacgaga tcggcccgat gggcggtgcc aaggtcgtgg ccaagtcctg ggtggaccct     180
gagtaccgca agtggctcga agaggacgcg acggccgcga tggcgtcatt gggctatgcc     240
ggtgagcagg cacaccaaat ttcggcggtc ttcaacgact cccaaacgca tcacgtggtg     300
gtgtgcactc tgtgttcgtg ctatccgtgg ccggtgcttg gtctcccgcc cgcctggtac     360
aagagcatgg agtaccggtc ccgagtggta gcggacccct gtggagtgct caagcgcgat     420
ttcggtttcg acatccccga tgaggtggag gtcagggttt gggacagcag ctccgaaatc     480
cgctacatcg tcatcccgga acggccggcc ggcaccgacg gttggtccga ggaggagctg     540
acgaagctgg tgagccggga ctcgatgatc ggtgtcagta atgcgctcac accgcaggaa     600
gtgatcgtat ga                                                         612

<210> SEQ ID NO 2
<211> LENGTH: 203
<212> TYPE: PRT
<213> ORGANISM: Rhodococcus rhodochrous

<400> SEQUENCE: 2

Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190
```

Ser Asn Ala Leu Thr Pro Gln Glu Val Ile Val
            195                 200

<210> SEQ ID NO 3
<211> LENGTH: 690
<212> TYPE: DNA
<213> ORGANISM: Rhodococcus rhodochrous

<400> SEQUENCE: 3

```
atggatggta ccacgacac aggcggcatg accggatacg gaccggtccc ctatcagaag    60
gacgagccct tcttccacta cgagtgggag ggtcggaccc tgtcaattct gacttggatg   120
catctcaagg gcatatcgtg gtgggacaag tcgcggttct ccgggagtc gatggggaac   180
gaaaactacg tcaacgagat cgcaactcg tactacaccc actggctgag tgcggcagaa   240
cgtatcctcg tcgccgacaa gatcatcacc gaagaagagc gaaagcaccg tgtgcaagag   300
atccttgagg gtcggtacac ggacaggaag ccgtcgcgga gttcgatcc ggcccagatc   360
gagaaggcga tcaacggct tcacgagccc cactccctag cgcttccagg agcggagccg   420
agtttctctc tcggtgacaa gatcaaagtg aagagtatga acccgctggg acacacacgg   480
tgcccgaaat atgtgcggaa caagatcggg gaaatcgtcg cctaccacgg ctgccagatc   540
tatcccgaga gcagctccgc cggcctcggc gacgatcctc gcccgctcta cacggtcgcg   600
ttttccgccc aggaactgtg gggcgacgac ggaaacggga agacgtagt gtgcgtcgat   660
ctctgggaac cgtacctgat ctctgcgtga                                    690
```

<210> SEQ ID NO 4
<211> LENGTH: 229
<212> TYPE: PRT
<213> ORGANISM: Rhodococcus rhodochrous

<400> SEQUENCE: 4

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ala Gly Leu Gly Asp Asp
            180                 185                 190

```
Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
        210                 215                 220

Tyr Leu Ile Ser Ala
225
```